(12) United States Patent
CasañGiner et al.

(10) Patent No.: US 8,337,900 B2
(45) Date of Patent: *Dec. 25, 2012

(54) REVERSE-PHASE MICROCAPSULES FOR ACTIVE INGREDIENTS, SIMPLIFIED PROCESS OF MANUFACTURE THEREOF AND COMBINED FORMULATION WDG-CS, ZC, EC-SC, AND CX

(76) Inventors: Victor CasañGiner, Ebenfurth (AT);
Miguel Gimeno Sierra, Ebenfurth (AT);
Barbara Gimeno Sierra, Ebenfurth (AT)

(*) Notice: Subject to any disclaimer, the term of this patent is extended or adjusted under 35 U.S.C. 154(b) by 444 days.

This patent is subject to a terminal disclaimer.

(21) Appl. No.: 12/225,889

(22) PCT Filed: Mar. 29, 2007

(86) PCT No.: PCT/EP2007/002809
§ 371 (c)(1),
(2), (4) Date: Sep. 30, 2008

(87) PCT Pub. No.: WO2007/112933
PCT Pub. Date: Oct. 11, 2007

(65) Prior Publication Data
US 2009/0053271 A1    Feb. 26, 2009

(30) Foreign Application Priority Data

Mar. 30, 2006   (EP) .................................. 06006748
Nov. 23, 2006   (EP) .................................. 06024299

(51) Int. Cl.
| | |
|---|---|
| *A01N 25/28* | (2006.01) |
| *A01N 59/20* | (2006.01) |
| *A01N 63/00* | (2006.01) |
| *A61K 9/50* | (2006.01) |
| *A61K 8/02* | (2006.01) |
| *A61K 35/74* | (2006.01) |
| *A61K 33/34* | (2006.01) |
| *A61K 8/23* | (2006.01) |
| *A23L 1/30* | (2006.01) |

(52) U.S. Cl. ........ 424/490; 424/408; 424/402; 424/637; 424/93.4; 424/648; 426/648; 504/117; 504/187; 504/359

(58) Field of Classification Search ........................ None
See application file for complete search history.

(56) References Cited

U.S. PATENT DOCUMENTS

| | | | |
|---|---|---|---|
| 4,534,783 A | | 8/1985 | Beestman |
| 6,039,966 A | * | 3/2000 | Kostka et al. ................. 424/405 |
| 6,113,935 A | | 9/2000 | Rodson et al. |
| 6,359,031 B1 | | 3/2002 | Lykke et al. |
| 2002/0086045 A1 | * | 7/2002 | Wang ............................ 424/408 |
| 2002/0115569 A1 | * | 8/2002 | Schnabel et al. ............. 504/310 |
| 2003/0161856 A1 | * | 8/2003 | Tandt et al. ................... 424/405 |
| 2005/0277549 A1 | * | 12/2005 | Seitz et al. .................... 504/359 |

FOREIGN PATENT DOCUMENTS

| | | |
|---|---|---|
| DE | 108 760 | 10/1974 |
| WO | WO 00/27519 | 5/2000 |

OTHER PUBLICATIONS

Wright et al. (In Advances in Pesticide Formulation Technology; Scher, H.; ACS Symposium Series; American Chemical Society: Washington, D.C. (1984)).*

* cited by examiner

*Primary Examiner* — Patricia A Duffy
*Assistant Examiner* — Garen Gotfredson
(74) *Attorney, Agent, or Firm* — Vedder Price PC

(57) ABSTRACT

Disclosed are microcapsules and processes of microencapsulation of water soluble or water dispersible compounds by reverse-phase microencapsulation and ways to combine them with other oil soluble or oil dispersible compounds in suitable formulations that yield tiny microcapsules and a very homogeneous distribution of particle size. Multiple combinations of these reverse-phase microcapsules are disclosed, including in combination with normal-phase microcapsules in order to create a Capsule Mixed Suspension (CX) where an outer oil phase or, alternatively, a water phase contains microcapsules of two types: those with a core of water and active ingredients dissolved or dispersed therein, and those with a core of oil and active ingredients dissolved or dispersed therein. Water Dispersible Granules (WDG) and Emulsion Concentrates (EC) and Suspension Concentrates (SC) combinations with the reverse phase microcapsules are also successfully performed.

37 Claims, 4 Drawing Sheets

Figure 1. Particle size distribution of formulation ZC of Example 7
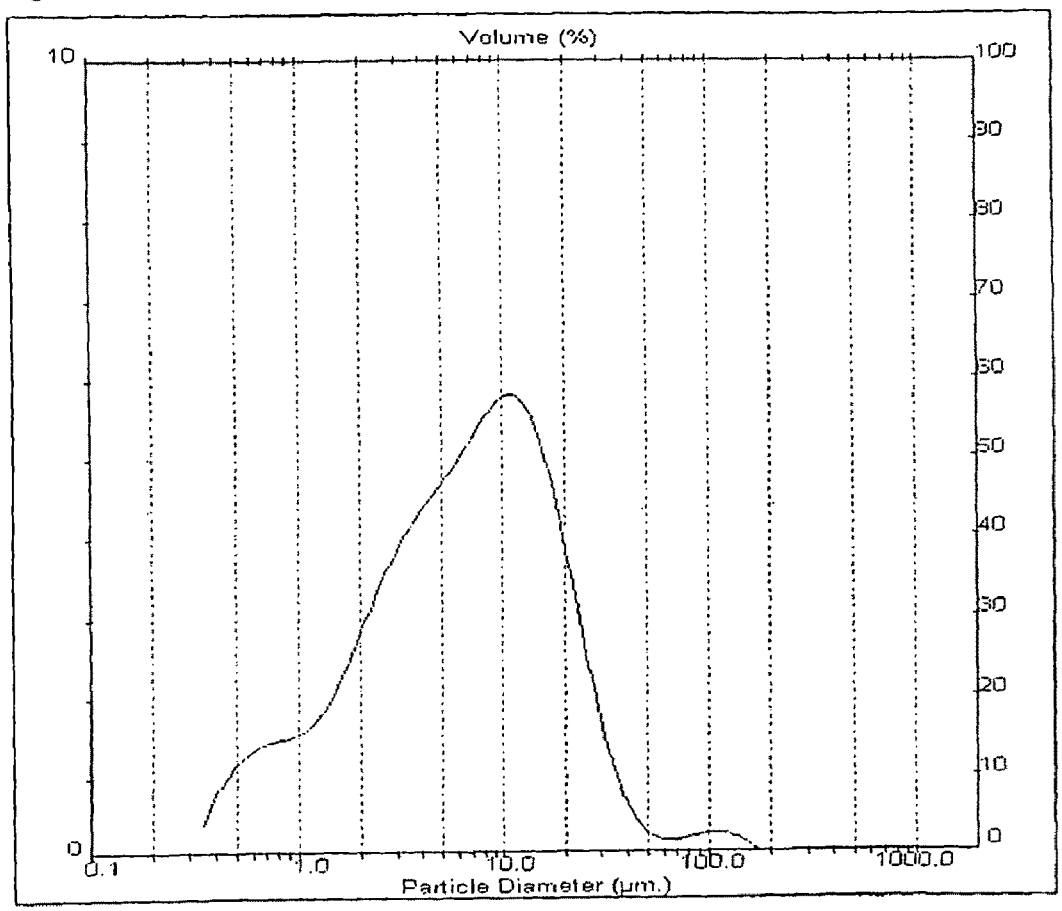

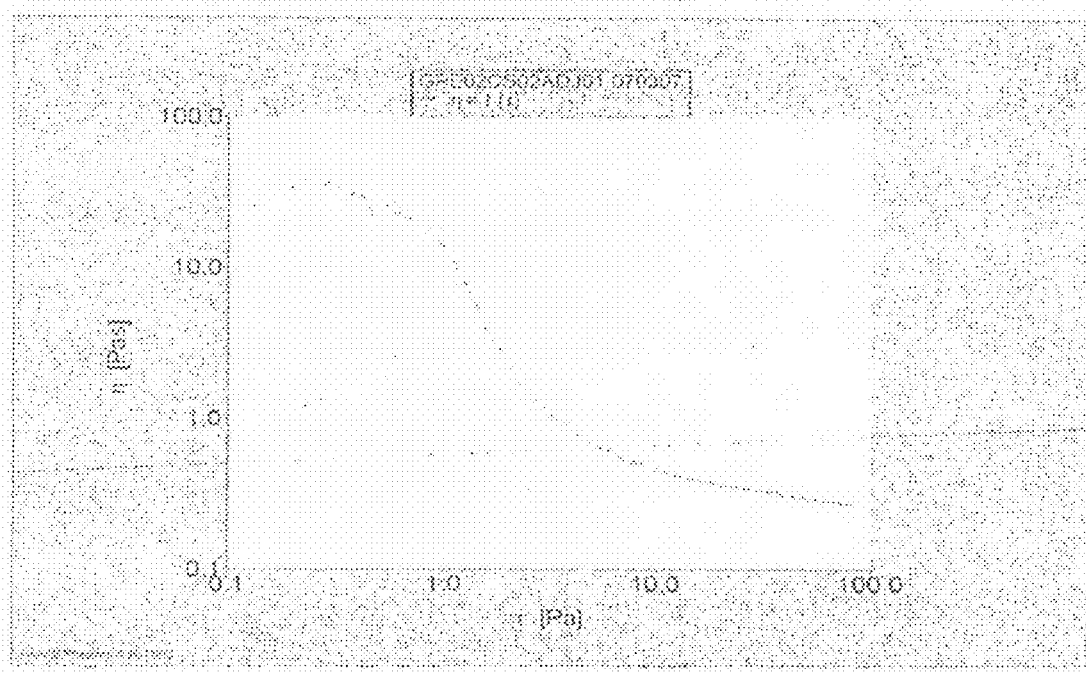

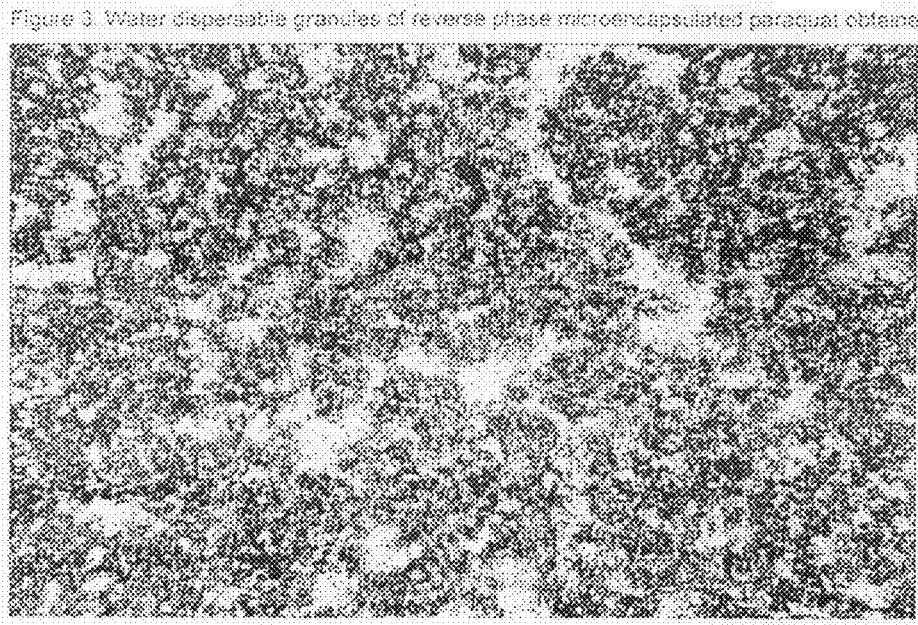
Figure 3. Water dispersible granules of reverse phase microencapsulated paraquat obtained in Example 10

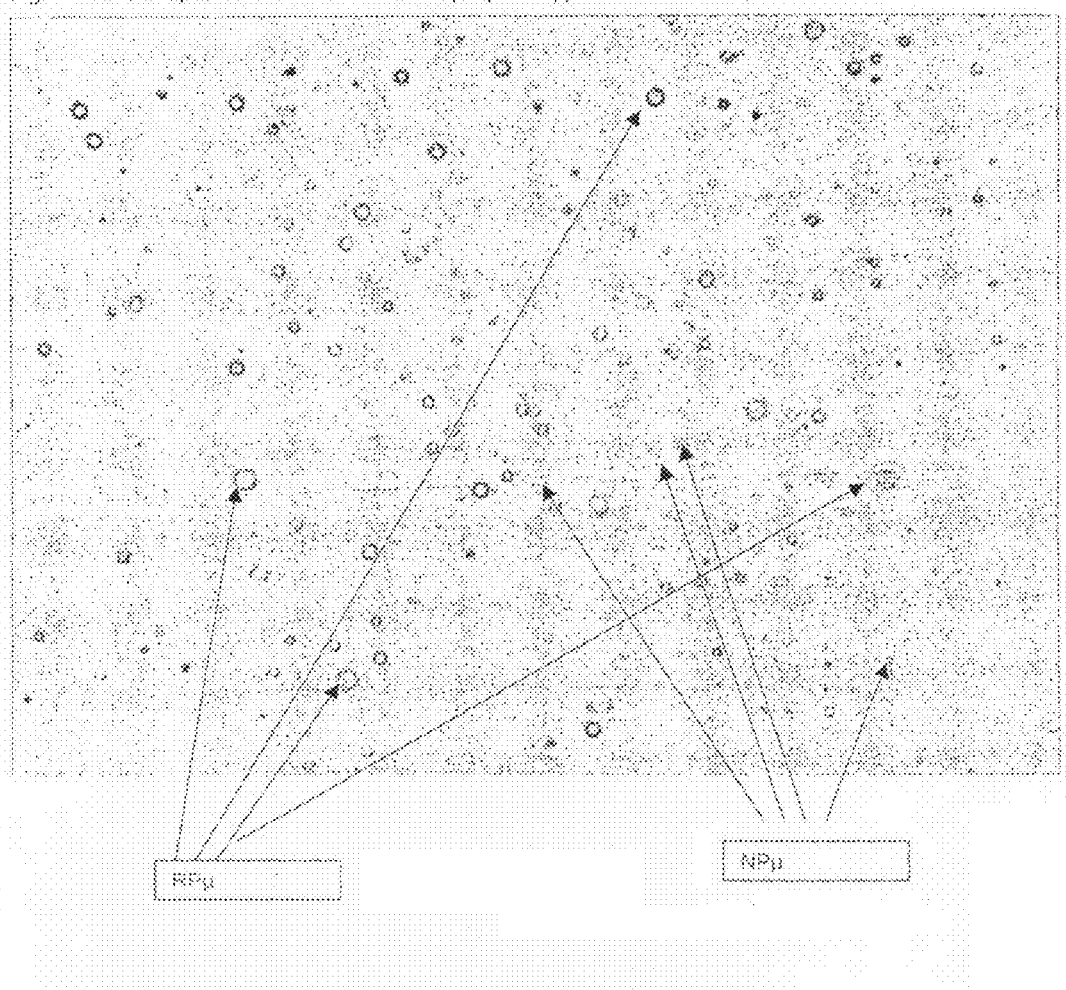

REVERSE-PHASE MICROCAPSULES FOR ACTIVE INGREDIENTS, SIMPLIFIED PROCESS OF MANUFACTURE THEREOF AND COMBINED FORMULATION WDG-CS, ZC, EC-SC, AND CX

FIELD OF THE INVENTION

The invention is in the field of microencapsulation, particularly in the field of microencapsulation of water soluble active ingredients in true microcapsules. The field of formulation of agricultural products is also addressed herein.

BACKGROUND OF THE INVENTION

The present invention regards microcapsules where a water phase is in inside the core together with biologically active ingredient(s), simplified process of microencapsulation and mixed formulations (capsule suspension plus suspension in oil, capsule suspension plus suspension concentrate, etc) and uses thereof. Further, here is described in full for the first time a usable agricultural formulation type that we called Capsule Mixed Suspension (proposed CX for a new two-letter code of international classification of formulations) characterized in that the formulation contains: i) a water or oil continuous outer phase ii) microcapsules containing an oily core with oil-soluble active ingredients and iii) microcapsules containing a watery core with water-soluble active ingredients iv) suitable coformulants, in particular surface active compounds.

The unitary concept of this invention is the reverse microencapsulation of water soluble (or dispersible) materials—active ingredients or a.i.—.

The technique of microencapsulation is well known in many fields. One field of special interest for the inventors is agrochemistry (any type of chemical compounds that are used in agriculture to improve the benefits of the farmer, including herbicides, fungicides, insecticides, raticides, semiochemicals, viricides, molusquicides, etc). However fields as cosmetics, medicine, pharmaceutics, etc., may take profit of the same microcapsule's and processes. For simplicity we will focus on agricultural uses.

The a.i. referred herein is in any of its forms, as long as it achieves a biologically technical effect, Traditionally the a.i. (in short, a.i., the use of the term "a.i." is used in plural, unless it is explicitly understood that is singular by the context) is referred as to the molecule (or moiety of the molecule) with herbicide, insecticide, attractant, etc. activity. For example, in an herbicide composition, the a.i. would be the molecule having herbicidal activity; in a cosmetic preparation, a fungicide that is part of the formulation and is inside the microcapsules would be an a.i., although such formulation may not be directed primarily to have antifungal effects (maybe is used for anti-wrinkle effect). The a.i. can be considered as well a safener or penetrator (e.g., fatty alcohol ethoxylates for "fop" herbicides) in a herbicidal composition or a penetrator enhancer for fungicides or herbicides (e.g. N-octyl-2-pyrrolidone), or a synergistic compound (e.g., a photosynthesis inhibitor that acts synergistically with the herbicide "main" a.i.; also a synergist in the case of insecticides of the pyrethroid type (e.g., pyperonyl butoxide). In other words, anything that has any type of biological activity either in its own or combined with another compounds, is to be understood as a.i. in the present invention. What would not be a.i. are, for example clays, buffers, surface active compounds in so far they do not affect significantly the biological effect of the a.i. and are present in the formulation as technological aids for the purpose of achieving usable formulation (e.g., stable and perfectly dispersable in the spray tank), etc.

The vast majority of known (true—it is said, those that have a wall that makes a physical separation of the a.i. from the continuous phase, to the contrary of those non-true "microcapsules" made by matrix encapsulation) microcapsules in the agrochemical field have in their core (discontinuous phase) a water-insoluble phase, it is said, the content of the microcapsule is oily, unpolar, substantially insoluble in water, and the microcapsules are dispersed in water (continuous phase). Inside the core may be solids or dispersed materials. Most of the prior art discloses microcapsules where the oily a.i.(s) is inside the microcapsule. We refer to it as normal microencapsulation or normal phase microencapsulation (NPµ in short).

However, there are many limitations as to form microcapsules where the continuous media is oily and the core contains water with water-soluble a.i. This is usually referred as reverse phase microencapsulation (RPµ in short). Patents dealing with RPµ, but providing rather different solutions are U.S. Pat. No. 6,531,160 (reactive wall forming materials not suitable for the purposes of this invention), U.S. Pat. No. 6,534,094 (biodegradable polymer, undesired for our addressed problems, since we need a wall strong to weathering conditions) or U.S. Pat. No. 6,572,894 (biodegradable wall as well).

The prior art shows an overwhelming presence of NPµ patents and scientific papers over that of RPµ. The state of the art presents a very restricted ways as how to produce RPµ. The use of oil soluble isocyanates or urea/melamine formaldehyde resins is the conventional way of performing NPµ. In the prior art, for achieving RPµ, the chosen wall forming materials must be in the water phase—or at least part of them—at the beginning of the process, therefore leading to undesired degradation of some a.i. due to the reactive nature of these water-soluble wall forming materials (e.g., polyols, wherein the hydroxyl group is free to react), difficulting the full reaction of wall forming materials and leading to microcapsules of 30-100 µm, bigger and more inhomogeneous than those obtained in this invention (see Example 10, CEI).

After producing the RPµ, the microcapsules must be mixed with the appropriate coformulants in order to obtain a functionally usable form of the microcapsules (e.g., addition of dispersants, wetters, skin UV-protectors . . . ). Normally the NPµ microcapsules are formulated in a water phase (e.g., capsule suspensions for agriculture) or after a drying process yielding water dispersable granules. Therefore, a need of different coformulants for the RPµ process and for the "second" process of formulation may cause logistic problems, especially to small companies wherein the availability of highly special chemicals (coformulants for NPµ or RPµ) is limited.

One problem addressed in this invention is to obtain in the same commercial formulation NPµ and RPµ. Note that not even one product in the market has ever had this particular feature (double-beneficial encapsulation of water and oil soluble a.i.).

One of the main problems to be solved when performing a microencapsulation (if not the most important problem) is to choose the right wall forming materials in order that they:

do not react with the a.i. or coformulants, either by the presence in the same initial water phase or by its lack of reactivity towards the chosen a.i.

do polymerize in a controlled way do not leave unreacted compounds or toxic compounds after polymerization do form a polymer with the appropriate thickness, porosity and hydrophobicity to allow the desired controlled release of the a.i.

do permit that the size of the microcapsules is sufficient small for a correct functionality the distribution of the size to be uniform This is achieved in this invention by a purposive selection of wall forming materials. The selection of the wall forming materials according this invention has been done with due account of preserving all the needs state above and, moreover, are appropriate for the much less usual reverse phase microencapsulation. Our selected wall forming materials allow not only such needs but also allow to microencapsulate a.i. in a high loads without the use of PVP polymers, also, a very homogeneous particle size distribution, and a very low amount of unencapsulated material. The use of glycoluril resins makes the process much less dangerous in terms of human toxicology in front of prior art use of monomer isocyanates (with high toxic profile and volatility). The use of glycoluril resins also makes the capsules more elastic and resistant to rupture by stresses during the production and afterwards (e.g., filling machines).

The problems addressed by the invention are several, although the invention can be formulated as to solve other problems as well, implicitly existing in the RPµ process.

The first problem is to find a reliably, simple and effective process of RPµ having microcapsules with small and homogeneous particle size and appropriate porosity. Other problem addressed is to be able to simplify the process of formulating for agriculture the RPµ product in such a way the need of different types of raw materials for the formulation plant is reduced to a minimum, for logistical and economic reasons. Also we address the need of avoiding or reduce to a minimum the degradation of the a.i. during the process (or even during storage) due to undesired side reactions. Also, we look for the combination of labile water—and/or oil-soluble a.i. in the same formulation. Obtaining a dry and stable and functional formulation of microcapsules made by RPµ, eventually with oil soluble a.i. incorporated in the dry formulation, is also one of our targets. Here is presented for the first time fully functional agricultural formulations wherein the two types of microcapsules are combined (the CX). There is no commercial product containing combined capsule suspensions (namely, NPµ and RPµ). The prior art shows enabling disclosures of formulations of microcapsules containing water phase in the core, or, always alternatively, oil phase in the core, but never before an enabling disclosure of a formulation containing simultaneously two types of microcapsules with a watery-core and an oily-core. It is highly surprising that this need has been never solved during more than 40 years after the first microencapsulation processes appeared and the increased efforts in the Agro industry to develop new formulations (reducing the investment in searching new molecules). It is uncontestable that this invention provides a big step forward in the field of formulation, at the view to the increased patents of the field of formulation and microencapsulation in the last years, and the fact that no patent addresses this problem of microencapsulating oil and water soluble a.i. with two different techniques and combine the final products. The invention solves these problems in the following way:

Providing a new process of RPµ with the use of determined wall forming materials, coformulants—those disclosed herein may be interchangeable with similar ones as far as the functionality is the same (e.g., with the same HLB and solubility properties) and preferably the molecular structure is similar—, and selective ratios, conditions of reaction and treatment (formulation) of the solution microcapsules formed.

Simplifying the process of RPµ in such a way that the same coformulants that are used in the step of formulation (same coformulants for different types of finished formulations). We refer to Example 1 to understand better this solution, where a RPµ Capsule Suspension (CS) formulation is formulated with the same coformulants as a combined CS-EC formulation (Capsule Suspension+Emulsion Concentrate).

Obtaining a very reliable process of RPµ with a sharp distribution of the microcapsule's size without the need of use prior art coformulants deemed essential till now for RPµ (e.g., polymers of the type of polyvinylpyrrolidone—PVP—) and without the need of adding any wall forming material in the water phase initially prepared, by means of choosing oil soluble wall forming materials and avoiding the contact of any water soluble wall-forming material (that may be present) until at least the emulsification step, wherein the contact of water soluble ingredients is reduced to a minimum (seconds or minutes at discrete intervals under agitation).

Microencapsulating by RPµ the water soluble (or dispersible) a.i. and having the oil soluble ingredient dispersed or dissolved in the continuous oil phase, with the processes already envisaged above and later mixing with NPµ.

Drying the formed microcapsules, both with a water soluble a.i. as the only a.i.; and also combination of water soluble a.i. with oil-soluble a.i., the latter being outside of the microcapsules. It cannot be assessed beforehand if our RPµ would be stress-resistant to spray drying.

Formulating the RPµ in such a way that can be incorporated with other formulations containing NPµ, providing a completely new approach in the agrochemistry field of formulations—there is not even an international code (e.g., used by the FAO or by the BCPC) for the type of formulations CX—.

We take a closer view of the prior art at the view of the problems cited.

U.S. Pat. No. 3,464,926 and U.S. Pat. No. 3,577,515 (Van de Gaer et al., Pennwalt Corporation) are pioneer inventions in the field of microencapsulation. As shown in FIGS. 1 and 2 of U.S. Pat. No. 3,464,926 and description thereof, the process is far complicated using flows and industrially complicated paths for the reactants to travel, economically very costly nowadays to bring into practice. Further, that patent refers only to microencapsulation of pesticides (diazinon and malathion) in "normal" phase, namely, oil in water, where the oil-soluble insecticide remains inside the microcapsule.

The RPµ is described in U.S. Pat. No. 3,577,515 Example 15, with the use of petroleum ether, carbon tetrachloride, talc, tetraethylene pentamine, calcium hydroxide, water, and dimer acid chloride, being the wall formed by the reaction of dimer acid chloride with tetraethylene pentamine. This (reactants, microcapsules formed, and process) process is rather different than the one described in the present invention, where, for example, we make no use of acid chlorides (highly reactive and likely to degradate a.i. to react to form the wall. No mention of the use of the RPµ for any agrochemical use is suggested in the case of water in oil microencapsulation, either the recommended sizes for a good performance in the final application in the field of such microcapsules or release rate characteristics.

The inventors have observed that, contrary to what is described in the closest prior art U.S. Pat. No. 4,524,783, where to form to polyurea wall to microencapsulate the water soluble compounds they use necessarily polyols [Examples 2, 3, 4, 6, 7, 8, 9 and 10] or polyamines [Examples 1 and 5] in the water phase), there is no need of using any amine or any alcohol or any further compound in the water phase to achieve a the RPµ according to the present invention. Having wall forming materials in the water phase provokes eventually undesired side reactions with the a.i. (this fact is so obvious for a skilled in chemistry that we do not provide more information on this regard). The present invention solves this problem "isolating" the a.i. in the water phase. According to the present invention, the microencapsulation may be carried out with a water phase that only contains the water soluble compounds(s) (a.i.) and water. This suppressive possibility of the removal of any additional compound in the water phase is beneficial for the stability of the water soluble compound(s) to microencapsulate, since the reactions of decomposition or just any kind of interference, are avoided by virtue of "isolating" the water soluble-a.i.(s) in a phase, leaving all the rest of the compounds in the other phase (oil phase).

One of the problems addressed in the present invention is to provide a water phase free from wall forming materials (if needed so) that may interact with the water soluble a.i.(s) to microencapsulate. All prior art cited above use part of the wall forming material to be in the oil phase, U.S. Pat. No. 4,534,783 makes use of diols in the water phase to react with the adipyl chloride (in example 4) or with the 1,6-Hexamethyl-enediisocyanate in example 3, or the amines in example 5, etc. U.S. Pat. No. 6,113,935 uses in wall forming materials in the water phase; in Table 1 (examples 2 to 8) the prepolymeric water forming material in the water phase is WS-351-380, or even urea/formaldehyde in the example 1.

U.S. Pat. No. 6,359,031 (Lykke et al.) performs a RPµ process by virtue of using carboxy-functional polymers to associate with amine functional reactive monomers in order to avoid that the non-protected (by carboxy groups) polymers are dispersed in the oil phase—remarking our addressed problem of undesired side reactions due to reactivity of wall-forming materials—. This solution is far complicated to perform, due to the cost of functionalizing with carboxy groups the water soluble polymers (implying lack of commercial sources or high prices of proposed polymers). This solution is appropriate for high-priced final microcapsules, as those described therein for enzymes, but such solution, as of today, is not viable for industrial application in the field of agrochemistry. Moreover, the extremely complicated modification of the polymers in order to achieve RPµ, when compared to this invention, makes more suppressive and inventive the easy solution proposed in the present invention. Also exists the possibility that these carboxy-protected polymers (the carboxy group or reduced aldehydes/ketones or alcohols) react with the water soluble a.i.(s).

U.S. Pat. No. 6,113,935 (Rodson and Scher, Zeneca Ltd.), published in 2000, still addresses the microencapsulation providing a water phase containing the reactive wall forming materials. This approach is preferentially avoided in the present invention, to avoid any side reaction in between the products to microencapsulate and for the first time here allowing a reverse microencapsulation with the use of only oil soluble wall forming materials. The presence of urea or melamine formaldehyde polymers in the water phase makes more difficult the completion till the end of the wall forming reaction, as well explained in U.S. Pat. No. 6,113,935 A1, col. 5: "As the polymer wall becomes more rigid, contact between the active groups on the [water-soluble] prepolymer becomes increasingly more difficult." This chemical scenario is completely reversed in our case. Since the wall forming materials are in the oil phase, the increased thickness of the wall will not prevent that the rest of the material self-polymerizes. When in U.S. Pat. No. 6,113,935 is said that the polymerization reaction is "self-terminating" is not due to a perfect availability of wall forming materials to react completely (it is not desirable to have rests of toxic unreacted wall forming materials in the final formulation), rather to the impossibility due to the growth of the wall thickness of complete reaction of the wall forming materials. Therefore, in U.S. Pat. No. 6,113,935, it is said "the reaction is self-terminating and is generally allowed to run to completion", provided this is interpreted in the light of the previous sentence where it is explained that this completion is due to the difficulty of the active groups of the water soluble prepolymer to really react completely. In our microencapsulation process, by virtue of the presence of the wall forming materials in the oil phase, there is indeed a completion of the reaction thanks to the absolutely complete reaction of the wall-forming materials (to the difference of U.S. Pat. No. 6,113,935, where the "completion" or "finishing" is due to unavailability to react more than the limit given by the wall thickness). Moreover, U.S. Pat. No. 6,113,935 system does not provide a solution to use the same process/components (of, e.g., Adjustment Mixtures A and B from our Example 1) for producing agrochemical formulations that may later be transformed easily in a combined formulation, as the solution offered in the present invention. No hint is provided as to formulate RPµ with NPµ.

It must be acknowledged that from a scientific point of view, the specialized literature is a source of guarantied knowledge for the state of the art, in between other things, because are peer reviewed publications, the prestige and the scientific correctness of the writer is in play and this is the way, how the scientist and technicians obtain fairly "trusted" information sources. We find in the book "Chemistry of Crop Protection" (Edited by Voss and Ramos, from the recognized Publisher Wiley-VCH, ISBN 3-527-30540-8) that the solution proposed by the inventors of the present patent goes against any expectation for the skilled in the art; namely, our proposal of using the wall forming materials only in the oil phase is disregarded as possible by the recognized microencapsulation expert George B. Beestman—inventor of one of the few RPµ and process, U.S. Pat. No. 4,534,783—, in pg. 273 of that book: "To prepare the reverse phase W/O (Water-in-Oil) emulsions care must be taken to select monomers that will remain in the dispersed water droplet during the emulsion stage. If the monomers diffuse from suspended droplets into the continuous phase polymerization will happen throughout the emulsion and not at the interface as intended. No microcapsules will be formed". He insists later in the same paragraph that in a process where amines participate, the microcapsules would have not been produced. The relatively new book (edited in 2003), used as standard reference in this field, does not give any hint into initiating the emulsification process without any compound in the water phase, lesser to provide the catalyst (in our case eventually a cycled azo compound) after emulsification has began, rather teaches away from the solution proposed. This inventiveness shown in the present application must be taken into account when considering that the closest prior art available is a patent of the author that teaches away from our solution proposed (Beestman shows a RPµ for water soluble agrochemicals). In the same chapter of Beestman, a mention of in-situ polymerization is made, but this time no reference of a possible formation of a RPµ is made using this type of polymerization (in fact, the only envisaged methods in the patent literature of performing a RPµ are those using the wall forming material either only in the water phase or in both oil and water phases, but not only in the oil phase as addressed in this invention in its preferred embodiment).

Note that according the invention, it is not addressed only that the water phase contains no wall forming material, rather, that in our aim to provide a simplified process of production of reverse phase microcapsules for further addition of other components or transformations in the formulation types—e.g. from a Capsule Suspension (CS) to a CS plus suspension concentrate (SC)—. Although we have found that one of the preferred embodiments is highly surprising over the state of the art, in the sense of the placing wall forming materials in the oil phase, nothing prevents the skilled in the art to use other features of this invention with traditional RPµ with wall forming material in the oil phase, as long as other benefits of this invention are achieved (e.g., combined RPµ and NPµ (CX formulation)). Then, the disclosure of this invention also embraces embodiments that have wall-forming materials in both phases, as a less attractive alternative, but possible. In this case it is needed that any material present in the water phase is inert with regard the a.i. and other components of the (initial) water phase. The term "inert" is well defined and clear in this invention: the water-soluble wall forming materials must not react, in the presence of water, and in the same proportions that are used in the water phase preparation of the process described herein, with the water-soluble a.i.(s) chosen, that are in the water phase.

These notes are needed to emphasize that the present invention solves the main problem of finding an improved process of microencapsulation of water soluble or dispersible a.i., and the partial problems of facilitating logistical needs and combinations of the microcapsules formed. Each of these partial problems has its own solution that may be used independently, with the common inventive concept of new RPµ applications. The same applies to the other partial problems mentioned above.

The invention comprises—when isolating its application in agrochemistry—the combination in a single formulation, of at least a microencapsulated water soluble agrochemical (preferably glyphosate and/or sulfosate and/or glufosinate) combined with an oil soluble insecticide outside the microcapsules (preferably sulfonylureas and/or sulfonamides) or in normal phase microcapsules, in such a way that all the a.i. remain stable, and optionally drying the resulting combination to obtain water dispersable granules containing RPµ and NPµ encapsulated (also non-encapsulated) sulfonylureas. Some preferred embodiments including sulfonylureas emanates due to the well-known instability of sulfonamides, and the wide use of glyphosate, sulfosate and glufosinate. Surprisingly, the inventors have realized that the process to microencapsulate water soluble herbicides herein disclosed, may be continued with the addition in the oil phase of sulfonylureas without any detriment to the functionality of the first microencapsulated water-soluble agrochemical or the subsequently added oil soluble material. Therefore the invention provides using the same process, either RPµ-water-soluble agrochemical (e.g. glyphosate) or, if desired, RPµ-water-soluble agrochemical plus oil soluble agrochemical (free or NP-microencapsulated).

It must be noted that the state of the art processes for NPµ, allow to have dry microcapsules containing oily agrochemicals in the core of microcapsules. These microcapsules can be added (dispersed) in the continuous phase of a RPµ formulation, in such a way at the end we have a formulation with water-soluble ingredients microencapsulated but also with oil-soluble ingredients microencapsulated. The dispersion in oil of such water-dried microcapsules can be done using dispersants of the type sodium alkyl naphthalene sulfonate, cresolformadehyde condensation products, EO/PO block copolymers or metal salts of fatty acid methyl taurides. As wetters for good dispersibility and suspensibility, we propose isotridecyl alcohol ethoxylate, sodium lauryl sulphate and metal salts of alkylsulfosuccinate, like sodium dioctylsulfosuccinate.

It is a question of obviousness that, in principle, any water soluble stable small organic molecule (e.g., agrochemicals, many medicines, alkaloids, oligopeptides) may be submitted to our RPµ and also that any oil soluble stable small organic molecule (e.g., agrochemicals, many medicines) may be added to the oil outer phase.

It is also a question of common knowledge for the skilled in the art which agrochemicals are not comprised in the scope in the patent, namely, those which for whatever reason would not be able to be used according the present invention: for example, an inorganic water or oil insoluble fertilizer could not fall in the scope of the invention if there is no reasonable mean to disperse it in the water or the oil phase; either any a.i. that would decompose by thermal degradation at the temperatures set out in the present invention. Namely, we claim that the invention is feasible in all the range of a.i. except those that can obviously not be submitted to our process. For the selection of the a.i., no undue burden is left to the skilled in the art, rather, only his/her normal knowledge in the area of microencapsulation and chemistry.

DETAILED DESCRIPTION OF THE INVENTION

The microencapsulation of the water soluble compound is performed having a water phase, wherein the water soluble compound (or mixture of water soluble compounds) is(are) dissolved, and an oil phase wherein the wall forming materials (polymers, prepolymers, oligomers or monomers), the catalyst(s), dispersants and coformulants are dissolved in an organic solvent.

Water Phase

According to this invention, the microencapsulation may be carried out with a water phase that only contains the water soluble compound(s) and water. The removal of any additional compound in the water phase before the emulsion step takes place is beneficial for the stability of the water soluble compound(s) to microencapsulate, since the reactions of decomposition or just any kind of interference, are avoided by virtue of "isolating" the water soluble a.i.(s) in a phase, leaving all the rest of the compounds in the oil phase. Is also possible to use water soluble wall forming materials, in so far other problems addressed in this invention are solved and provided that the water soluble wall forming materials do no react with the a.i.

Oil Phase

Solvent: Any solvent able to dissolve the a.i. (whether a single a.i. or a combination of oil-soluble a.i.) is able to be used, as far is inert for the a.i. Usual solvents are vegetal or mineral oils, aromatic, paraffinic or aliphatic hydrocarbons such as Solvesso® 100, 150 or 200 (aromatic hydrocarbon solvents containing dialkylbenzene and trialkylbenzene manufactured by Exxon Mobil Corporation), a Marcol® (light mineral oil), or an Isopar® (aliphatic hydrocarbon), including aliphatic, hydrocarbons that are aromatic and mixes thereof etc. More volatile solvents may also be used, as lower alcohols (e.g., butanol, hexanol, octanol), cyclohexanone, gamma-butyrolactone, N-alkyllactams, N,N-dimethylalkylamides or -amines, and in general, any solvent used in agrochemical products.

Wall forming materials: As wall forming materials we select a combination chosen at least from one of the two groups (preferably from both): a) isocyanates, preferably, an aliphatic isocyanate, preferably chosen from the group TMXDI, Cythane® 3174 [CYTEC], eventually, and/or an aromatic isocyanate (preferably chosen from TDI, MDI). The short names for isocyanates used in this invention are well known for the skilled in the art and common in the patent literature. b) glycoluril resins, preferably, Cymel® 1170 (a glycoluril resin alkylated with n-butyl), Cymel® 1.171 (glycoluril resin alkylated with methyl and ethyl), Cymel® 1172 (an unalkylated glycoluril resin) and Powderlink® 1174 (tetramethoxymethyl glycoluril) (from CYTEC Industries).

A preferred combination is to choose TMXDI and Cythane® 3174 (trimethylol propane) from group a) together with Cymel® 1170 of group b) with a ratio 10:1 to 1:10 in wt.-% of TMXDI to Cythane® 3174; preferably with a ratio in wt.-% of group a) to group b) from 15:1 to 2:1.

Catalysts: Any catalyst able to catalyze the polymerization reaction is able to be used. Dialkyltin fatty acids are preferred, in particular dibutyl tin laureate. Also a cyclic (di- or tri- or tetra-cyclo) (mono-, di-, tri-, tetra-)aza catalyst is used, preferably {1,8-}Diazabicyclo[5.4.0]undec-7-ene [in short, DBU]. The azacyclo catalyst may belong either to the initial oil phase or to the emulsion water in oil solution that is formed during the process (introduced dissolved in oil right after the beginning of the emulsification, this is our preferred solution, since better control of reaction is achieved). This way, it reacts (and is preferentially located) on the interface of the water and oil phases with the wall forming materials. The DBU is preferably used as a solution in the oil solvent, preferably from 5-50% in wt.-%. Any coformulant that is water soluble and may be functionally of interest for the final formulation might be added in the initial water phase (e.g., a dispersant for water-dispersed a.i. with low affinity for the chosen oil phase). In order to speed the reaction when using glycoluril resins, a catalyst of the type proton transfer catalysts (preferably of the type p-toluenesulfonic acid and derivatives) is recommended, although we have suppressively observed that is not necessary. The glycolurils are incorporated in the mixed polyurea-glycoluril wall without the need of these recommended sulfonic acids.

Coformulants: For the purposes of obtaining a water phase as "pure" as possible, the coformulants will preferably be oil soluble and be in the oil phase. However, inert coformulants may be added to the water phase as desired, as it can be the case of antifreeze agents (e.g., propylen- or diethylen- or polypropylene-glycol), pH adjusters, antioxidants, UV-protectors, etc. Preferably there will be used surfactants and dispersants, in the oil phase, of the type Atlox® 4914 (a water-soluble acrylic copolymer from Uniqema), Atlox® LP-6 (poly(12-hydroxy-octadecanoic acid-co-ethylenimine) or/and LP-1 (an anionic polymeric surfactant), and any conventional surfactants that may easily be found in catalogs (e.g., Clariant, ICI, Rodhia surfactant/dispersant catalogs) with similar functionality as those mentioned. For the purposes of achieving a good microencapsulation, no other coformulants are needed in our process. However, any further coformulants that may be needed for a good performance of the final formulation (e.g., wetters, binders, other dispersants, etc.) may be added in this oil or water phase, or, preferably, at the end of the process.

Emulsification-Microencapsulation Step

Once we have both oil and water phases, we just perform an emulsification step, that in laboratory conditions may be done with an Ultraturrax L4 at 30-95° C. for 2-20 minutes. After the first minute of emulsification, the azo catalyst is to be added slowly. At this stage the structure of the wall of the microcapsules is already initiated and partially terminated. The emulsion is left with gentle agitation (anchor stirrer, for example) at 40-80° C. for 30-240 minutes in order to cure the microcapsules. We already have the microencapsulated formulation of water soluble compound.

Formulation Step

If the final product is an agrochemical formulation, we need to add further components in order that the product will be emulsifiable in water. For this purpose we can use compounds of the type Atlox® G-5000 (polyoxypropylene/polyoxyethylene butanol copolymer), Dispersing Agent LFH® (tristyrylphenol polyoxyethylene phosphoric acid ester) made by Clariant, Atlox® MBA 13/8 (an alcohol ethoxylate surfactant), Attagel® 50 $(Mg,Al)_5Si_8O_{20}.4H_2O)$. (preferably in solution 10-90 wt.-%) and eventually more solvent.

At this stage we already have a fully functional agrochemical formulation ready to be use by the farmer (emulsification in the water tank and spray).

The applicant have invented this process in order that further combination with other oil-soluble agrochemicals is suppressively easy when using the process described above.

From the formulation obtained above, it can be just added the oil soluble a.i. (or mixture of a.i.) in pure form—if liquid—or preferably dissolved in the same solvent that constitutes the oil continuous phase described above.

This process allows the producer to convert easily a capsule suspension formulation (in reverse phase, namely with oil as continuous phase) into a mixture of a capsule suspension with an emulsion concentrate.

We have suppressively found that to the "microencapsulated in water phase"-material it can be added (as continuous phase) an oil suspension (e.g., by emulsification) of water-soluble material that has been previously milled and stabilized in the oil with the aid of coformulants (mainly dispersants for homogeneicity), namely, to for a suspension in oil+ capsule suspension formulation.

The water phase inside the microcapsules may contain water-insoluble a.i.s dispersed in such water phase, plus coformulants to stabilize the suspension. These are variants of the present invention that the skilled in the art may reproduce with common knowledge in the field. A need in the case of mixing water-soluble compounds with water-insoluble compounds that are milled (dispersed in the water inside the microcapsules) is that they are not chemically incompatible. In the case of addition of oil-dispersed a.i., the process described above is directly useful, since there is no way in which the oil-dispersed a.i. will go inside the microcapsules. In the case that is added in the initial water phase a water-dispersed a.i., care must be taken in order that during the emulsification process the water insoluble a.i. (intended to be inside the microcapsule) does not go into the oil phase: for this reason, only compounds that are insoluble in water, and at the same time insoluble (not readily soluble) in the chosen solvent (oil phase) are able to be incorporated according the present invention. Otherwise, we have seen that a high migration to the outer oil phase. In these cases of looking for a good dispersion in water, the better approach is to look for an oil phase wherein the water-insoluble a.i. is also not soluble. This may be the case where the a.i. is soluble in low molecular weight solvents (e.g., tebuconazole as a.i. in cyclohexanone) but is substantially insoluble in naphtha solvents (e.g., tebuconazole in Solvesso 100). In this case, the tebuconazole could be milled and suspended in the water phase (nitrogen atoms of tebuconazole show affinity for water) and would not go preferentially to the Solvesso 100, thus allowing the microencapsulation of both the water-soluble a.i. and the water-insoluble a.i. The selection of the oil phases that is the best for avoiding this migration of the milled water-insoluble a.i., is a routine task based on the selection of the oil phase solvent.

The possible formulations obtainable by this invention are provided in the following scheme:

active ingredients that are water soluble: ai-ws1, ai-ws2, ai-ws3, etc.

active ingredients that are oil-soluble: ai-os1, ai-os2, ai-os3, etc.

RPµ: reverse phase microcapsules (water and water-soluble a.i. in the core)

NPµ: normal phase microcapsules (oil and oil-soluble a.i. in the core

SC: a suspension concentrate in water of an oil-soluble a.i. milled and dispersed in water AM-SC: an Adjustment Mixture appropriate for emulsifying the RPµ into an SC (or viceversa) to form a RPµ-SC (=ZC).

AM-WDG: an Adjustment Mixture appropriate for creating water dispersable granules AM-EC: an Adjustment Mixture in which an ai-os1 is in the form of Emulsion Concentrate, that after mixing with the RPµ in oil produce an EC of RPµ, having both ai-ws1 and ai-os1.

AM-NP: an Adjustment Mixture added to a NPµ, appropriate for emulsifying an NPµ formulation into the RPµ in oil.

AM-NPX: an Adjustment Mixture appropriate for emulsifying an RPµ formulation into the NPµ in water.

CX: combined capsule suspension, namely, a combination in the same formulation of RPµ [containing ai-ws1] and NPµ [containing ai-os1].

CXw: CX wherein the continuous phase is water

CXo: CX wherein the continuous phase is oil

DRPµ: dry reverse phase microcapsules (after, e.g., spray drying of RPµ in oil)

AM-DRP: an Adjustment Mixture appropriate for drying (e.g., spray drying) RPµ into a fluid formulation of RPµ microcapsules (DRPµ)

AM-NRP: an Adjustment Mixture appropriate for drying (e.g., spray drying) NPµ into a fluid formulation of NPµ microcapsules (DNPµ)

a. RPµ with ai-ws1 in the core, dispersed in oil
b. RPµ+AM-WDG→(spray dry) [extrusion is an equivalent process]→WDG of RPµ with as-ws1
c. RPµ+SC+AM-SC→(spray dry)→WDG of RPµ with ai-ws1 and ai-os1
d. RPµ+AM-EC→RPµ-EC with ai-os1 together with a RPµ with ai-ws1
e. 1) RPµ+AM-NP→(addition to the oil in which the RPµ is present of a NPµ formulation)→CXw in watery continuous phase with ai-ws1 and ai-os-2, both a.i. being microencapsulated→(spray dry)→WDG-CXw
   2) NPµ-AM-NPX→(addition to the water in which the NPµ is present of a RPµ formulation)→CXo in oily continuous phase with ai-ws1 and ai-os-2, both a.i. being microencapsulated→(spray dry)→WDG-CXo
f. RPµ+AM-DRP→(drying)→DRPµ+NPµ→CXw
g. NPµ+AM-DNP→(drying)→DNPµ+RPµ→CXo In order to achieve a CX formulation, in the examples are given the preferred surfactants: they must satisfy that the RPµ to be mixed with a NPµ (or viceversa) are in a quantity from 1-50%, preferably 5-25% and more preferably 10-20% in the formulation to be combined. To mix a RPµ into a NPµ surfactants with high HLB are needed, with a HLB of 7-14, preferably 8-14 and more preferably 9-13. To mix a NPµ into a RPµ surfactants with low HLB are needed, with a HLB of 1-7, preferably 1-5, and more preferably from 2-5. As first choice, the skilled in the art trying to reproduce the invention should try the proposed surfactants in the concentrations set in the section Examples. When failing these trials, increase on the concentration of surfactants of 10% is to be tested, then selecting two or three similar surfactants (but with different molecular formula) with similar HLB. If this two short tests fail, then a surfactant (preferably with same formula but with changed number of ethoxylated/propoxylated mols) an increased or decreased HLB (respectively for mixing RPµ to NPµ and for mixing NPµ to RPµ) is to be tried. These basic and necessary adjustments, following these recommendations have been proved to work for at least 25 different combinations of a.i. and concentrations of a.i. by the inventors, therefore this process is deemed to be workable in all the claimed range of existing agrochemicals. In all these trials, the first choice solvent for the NPµ is of type naphtha, as second choice parafinic oils, and as third choice vegetable oils (preferably hydrogenated or partially hydrogenated). As a rule, the minimum deviation from the surfactants and solvents and wall forming materials, is preferred to be able to perform workable formulations.

In order to obtain water dispersable granules from CX formulations (or all the other possibilities mentioned in the invention containing RPµ) we have seen that the best procedure is to provide a matrix for absorbing the oil, with customary aids for drying for each batch, in particular for spray drying (by analogy, in the extrusion processes). The most preferred way to perform this step of drying RPµ or CX-containing formulations is by spray-drying, adding to the spray chamber absorbants or adsorbants of the type caolin, clays or carbohydrates (starches, carboxymethylcellulose, cyclodextrins; and derivatives, etc.) Again, the lesser deviation from the examples, the better results are expected.

We have suppressively found that most of the emulsifiers adequate for performing emulsification of oils into water may be used without any interference with the capsule suspension stability in the final CX formulation. Therefore, we include herein those surfactants appropriate for forming oil in water emulsions, as extensively explained in catalogs, e.g. that of Uniquema catalogs available on Internet (www.uniquema-.com) and in hard copy, cp/e/9-99/-/eur/02/1k (adjuvants) or cp/e/9-99/-eur/03/1k (Formulation additives). This is evidently not obvious, since the mentioned products are though not at all for emulsifying oil containing capsules, rather only to emulsify oils in water. No mention therein is made that capsule suspensions would be stable when emulsifying a RPμ formulation into a NPμ with high HLB surfactants (or the reverse for NPμ into NPμ with low HLB surfactants). Indeed, we believe that in our invention is for the first time shown the stability of microcapsules when mixing RPμ and NPμ (or viceversa) when using conventional surfactants.

For reasons of clarity, we will discuss in detail the invention related with the claims (each paragraph marked refers to the claim number pointed out).

§1 The invention provides microcapsules for controlled release of water soluble or dispersible compounds, preferably agrochemicals, characterized in that the microcapsule have a polymeric wall consisting in the in-situ reaction polymeric product of the only oil soluble material(s) selected from at least one of the groups i) or ii), more preferably at least one of each group, and most preferably one of each group:

i) at least a glycoluril resin, preferably a tetra-butoxylated glycoluril resin ii) at least an isocyanate, preferably an aliphatic polyisocyanate resin and, when chosen from both types, the ratio of ii) to i) is at the most 20:1 and at least 1:2 and the average size of the microcapsules is from 0.1 μm to 50 μm, preferably 1 to 5 μm, and the size percentile 90 of the microcapsules is at the most 200 μm, preferably 35 μm, when measured in dispersion in water in a laser diffraction apparatus, optionally of the type Mastersizer™.

It is quite relevant the term "oil soluble" materials, which form the wall: this means in the present claim that the wall forming materials are in the oil phase and only in the oil phase when performing the microencapsulation. However, this technical feature is reflected as well in the finished microcapsules (since the wall is formed only by oil soluble polymers) therefore we direct a claim to the product itself, not necessarily as a product by process claim.

The prior art in RPμ show that the wall forming materials must be selected from melamine-formaldehyde or urea-formaldehyde resins (as in U.S. Pat. No. 6,113,935, claim 1 a)) placed on the water phase or the polymer formed is a polyamide, polyurea, polyurethane, polysulfonamide, polyester or polycarbonate (as in U.S. Pat. No. 4,534,783), wherein the wall forming materials are also placed (at least some of them necessarily) in the water phase. The formation of a glycoluril-polyurea polymer for reverse phase microencapsulation is new, and provides advantages over the prior art. Repetition of example 10 of U.S. Pat. No. 4,534,783 yield microcapsules with a mean particle size of 74 μm with a percentile 90 of 398 μm. A further attempt to achieve smaller microcapsules with the basis of a polyurea wall, led indeed to smaller microcapsules, but then part of the IPA salt crystallized (about 13%) in the oil phase. Repetition of examples 2 and 8 of U.S. Pat. No. 6,113,935 lead to very big microcapsules (actually the denomination of microcapsules begins to be no more applicable) with a mean diameter of 289 μm and 310 μm respectively, with a percentile 90 at 1512 μm. It is clear that exists the need of small microcapsules that are able to be attached to the points of action of the respective compound (e.g., a fungicide or herbicide inside of microcapsules will perform better is the size allows a better attachment to the fungi or the leaves, and this is directly dependent with the size), further, for some cosmetic applications smaller microcapsules resist much better stresses due to mixing operations or even high pressure homogenization processes. Another advantage of the smaller size of microcapsules is that they have a faster release due to the higher surface provided by the smaller spheres (and in the case that a fast release wants to be avoided, our invention solves this increasing the percentage of wall forming materials over the total weight, in that way, the wall is thicker, attenuating the release, but with similar outer diameter).

Even more important is the homogeneicity of the microcapsules (that the maximum possible of the microcapsules are very close to the mean, namely, is a pronounced leptocurtic Gaussian distribution, in other words the peak showing microcapsules' count versus size is as sharp as possible (see attached particle size measurements). This homogeneicity is also fundamental to obtain a product with reliable functionality. While in the field of normal phase microencapsulation (NPμ) some of these problems have been solved, the special characteristics of the RPμ, led these needs not to have been solved till now. In order to make clear what is one of the multiple advantages of this invention, the size preferred must be in between 0.1 to 25 μm in average, and to have homogeneous, sharp distribution, the percentile 90 we recommend to be under 50 μm. Naturally, we obtain bigger microcapsules just by decreasing the amount of emulsifier and reducing the shearing stress during the emulsification step.

The material to be microencapsulated may be a single compound or a combination of compounds: e.g., in an herbicide formulation, diquat and paraquat; in a medicinal formulation against asthma, caffeine and theophylline and theobromine.

The compounds to microencapsulate must be water soluble or water dispersible, normally used at a concentration below the solubility limit of solubility the chosen compounds. However, the compounds may be over its solubility limit (therefore, part will be solubilized and part precipitated). The requirement for such embodiment is that the compound used over the solubility in water limit, especially the solid part, is thoroughly dispersed in the water with the use of commercial common water dispersants. This a routine task that can be accomplished by adding to the water phase a water-soluble dispersant and a previous milling of the water phase (or an aliquot of the water phase) in a conventional milling machine to the desired particle size.

Another requirement for the invention to be workable is that the solubility of this solid compound in the chosen oil phase is very low or at least lower than that in water. For example, acifluorfen-sodium (solubility in water about 60 g/L) could be formulated at 100 g/L in the core of the microcapsules, the 40 g/L that would be in solid form due to reaching the solubility limit should be not soluble, or few soluble in the oil phase. Therefore we could chose hexane as the matrix of the oil phase or even isooctanol, where the solubility is around 6 g/L. Due to the chosen initially water phase and the water-dispersants used, the water-dispersed acifluorfen-sodium will tend to stay in the water phase and not displace to the oil phase before the microcapsules are formed. It is contemplated that the a.i. is insoluble in water, and it is dispersed therein, but is at the same time insoluble—or at least less soluble than in water—in the oil phase. We will refer in this document as something "insoluble" or "substantially insoluble" when the solubility is lower than 1 g/L, with respect to the phase referred in each case. For example, we could mill the fungicide tebuconazole (insoluble in water) in water, and then use a unpolar solvent as the "matrix" of the oil phase (namely, majoritary compound of the oil phase, when used several unpolar solvents these considered together would be the matrix), provided that tebuconazole is also insoluble in such oil phase. As a example, we could chose hexane, wherein the tebuconazole has a solubility lower than 0.1 g/L.

Both microencapsulations of acifluorfen-sodium and tebuconazole have shown to work (homogeneous microcapsules of mean diameter of, respectively, 9 and 11 μm, and negligible presence of the a.i.s in the oil phase by, respectively, HPLC-UV and GC-FID analysis).

A further advantage of using glycoluril resins is that they, by chemical structure, are much less reactive than the conventional urea and melamine resins, therefore allowing a better control of the reaction when performed in industrial size.

We also claim:

§2 Microcapsules wherein the microcapsule have a polymeric wall consisting in the reaction of:
  i) a glycoluril resin, preferably a tetra-butoxylated glycoluril resin
  ii) an aliphatic polyisocyanate resin, preferably of the type Cythan® 3714, combined with TMXDI
  wherein in the polymerization reaction it is used at least a catalyst selected from one or the two the groups
  i) polycyclic azo compound, preferably [di-, tri- or tetra-] cyclo [mono-, di-, tri- or tetra-]aza catalyst, preferably a diazabicyclo catalyst, more preferably {1,8-}Diazabicyclo[5.4.0]undec-7-ene.
  ii) a non-nitrogenated oil-soluble catalyst, preferably dialkyl tin fatty acid ester, and more preferably dibutyl tin laurate preferably with one catalyst from each group and most preferably the combination of {1,8-}Diazabicyclo [5.4.0]undec-7-ene and dibutyl tin laurate In this case, we want to point out what is the preferred solution that we adopt, namely the combination of the said wall forming materials, and that the wall is formed (therefore the microcapsules is also characterize by that) with the aid of the mentioned catalysts. Further the selection of the catalyst i) is advantageous because we have suppressively noticed that if we add such catalyst right after the emulsification is begun, the catalyst is able to perform the wall forming reaction. Further, it is our best solution found to combine these two types of catalysts, another surprising effect of this invention, since what is prior art is to use one catalyst of one type, and not two catalysts as we propose optionally. The reaction is achieved equally by the use only of dibutyl tin laurate, but the size of the microcapsules is then increased by about 10%. Obvious variations of catalysts' structures also work in our invention (e.g., dibutyl tin stearate, triaza catalysts, tricycle catalysts, etc.), in any case is a question of elementary chemical synthesis knowledge to disregard which catalyst could not perform enough well the reaction.

§3 When applying the present invention to the field of agrochemicals, the preferred compounds to microencapsulate are selected from the list: acifluorfen-sodium, ammonium sulfamate, asulam-sodium, aviglycine hydrochloride, potassium bicarbonate, sodium bicarbonate, bilanafos-sodium, bispyribac-sodium, borax, bromoxynil heptanoate, sec-butylamine, cartap hydrochloride, chlormequat chloride, sodium chloroacetate, clofencet-potassium, clopyralid-olamine, copper sulfate, 2,4-D-dimethylammonium, 2,4-D-sodium, dalapon-sodium, 2,4-DB-sodium, dicamba, dichlorprop-potassium, dikegulac-sodium, dinoterb-diolamine, diquat dibromide, diquat dichloride, ferrous sulfate, flucarbazone-sodium, flupropanate-sodium, formaldehyde, formetanate hydrochloride, fosamine-ammonium, fosetyl-aluminium, fosthiazate, gibberellic acid, glufosinate-ammonium, glyphosate-isopropylammonium, glyphosate-trimesium, glyphosate-sodium, glyphosate-ammonium, glyphosate, guazatine acetates, GY-81, hexazinone, 8-hydroxyquinoline sulfate, hymexazol, imazalil sulfate, imazapyr, imazaquin-ammonium, iminoctadine triacetate, iodosulfuron-methyl-sodium, ioxynil-sodium, ioxynil, kasugamycin hydrochloride hydrate, maleic hydrazide, maleic hydrazide potassium salt, MCPA-sodium, MCPA-sodium, mepiquat chloride, mercuric chloride, mesosulfuron-methyl, mesotrione, metalaxyl, metalaxyl-M, metam-sodium, methamidophos, methomyl, methaldehyde, naptalam-sodium, nicotine, sodium o-nitrophenolate, sodium p-nitrophenolate, sodium 5-nitroguaiacolate, paraquat dibromide, paraquat dichloride, sodium pentachlorophenoxide, sodium 2-phenylphenoxide, phloxine, picloram-triisopropanolammonium, picloram-potassium, propamocarb hydrochloride, propoxycarbazone-sodium, pyrithiobac-sodium, streptomycin sesquisulfate, strychnine, 2,3,6-TBA, trichloroacetic acid, TCA-sodium, thiocyclam hydrogen oxalate, trifloxysulfuron-sodium, validamycin, chlordimeform hydrochloride, chlorphonium chloride, dehydroacetic acid, 2-methoxyethylmercury chloride, natamycin, potassium cyanate, prothiocarb hydrochloride, sodium fluoride, sodium hexafluorosilicate, TEPP; in any water soluble form, in any isomeric or stereochemical composition.

Not only this water soluble ingredients may be microencapsulated according the present invention: cosmetics and pharmaceutical a.i. water-soluble, and not readily reactive with the wall forming materials may be microencapsulated.

Although some of these compounds (active ingredient) are few soluble in water this solubility is acceptable for the purposes of the invention since this low solubility may suffice for bioactivity, in especial for those agrochemicals highly active at very low doses. However, the easier use, in the sense of higher dosage and no need of dispersion, of the present invention is for those compounds with solubility in water at least of 10% in wt.-%. It is to be understood that the list provides the most common chemical names of the a.i., in the most common form. Obviously, for this list, and for all other mentioned a.i. in this document (e.g., oil soluble a.i.), salts or the methyl derivatives or demethylated derivatives of mentioned compounds are explicitly included (e.g, glyphosate includes glyphosate-ammonium, glyphosate-isopropylammonium, glyphosate trimesium, and so on). What is important is that the biologically active part of the molecule represented by the abovementioned representative compounds is present in the derivatives. This also includes isomers and stereoisomers and different crystal forms. When the salt is soluble in water and the free (e.g. acid) form is insoluble in water, then, for the purposes of microencapsulation on claim 3, we refer only to the water-soluble forms.

§4 The invention is suitable as well for active ingredients not classified in the agrochemical field, as drugs or medicines, living or death organisms in any physiological state including spores or pollen, such as mycoplasmas, fungi, bacteria, virus, viroids, prions, yeasts, plants, or genetic material, cells, stem cells, cells for xenotransplantation, aminoacids, nucleic acids, DNA, RNA, proteins, aminoacids, vaccines or compounds directed for feeding purposes. There no specific feature in the present invention that prevents to be used for the mentioned purposes, except of the temperature and the shear stresses needed in our process. The skilled in the art is able to determine case by case when the invention has no application; e.g., for microencapsulation of heat sensitive cells or a protein that is both denaturalized and lose its biological activity at 40° C., temperature that is needed for the curing of the microcapsules.

The skilled can also determine when the chosen isocyanates or glycoluril compounds will result in degradation of the bioactive ingredients and therefore this invention cannot be used. In any case this is to decide in a case-by-case basis. There is an increasing need to formulate the abovementioned materials in the medical and biotechnological and chemical field. Up to now, microencapsulation of such materials has been done by completely different process, mainly by coacervation, because the inherent difficulty in obtaining reverse phase microcapsules. We are not aware of any public document that approach the solution of this problem with our microcapsules, lesser without our process, and the prior art, by avoiding systematically the in-situ true (namely, not sponge-type microcapsules) microencapsulation with wall forming materials in the water phase, teaches away from our solution. The closest prior art regarding this claim could be WO 89/04170, but they do not yield spherical "true" microcapsules, rather an amorphous and unhomogeneous organic matrix wherein the viruses ore bacterial spores are entrapped. Our experiments show that the reduced claimed size of the capsules 5-50 µm cannot obtained directly by an in-situ reaction where the wall entraps absolutely the water and water-suspended materials (as happens in our invention), rather, by spray drying the matrix (sponge-type capsules). Namely, only by spray drying such small size of the matrix-encapsulated materials can be reached (this is in agreement with WO 89/04170, wherein only example 11 show the (mean) particle size, after spray drying. On the other hand, the wall forming material of that invention (Eudragit, polyacrylates, etc.) are far different from the used in the present invention.

§5 The microcapsules so far described can be used in a dry or flowable form. A very easy way to perform this embodiment is to microencapsulate in a highly volatile solvent (e.g., octane) and after encapsulation evaporate the solvent by simple heating, preferably under vacuum. If this is to be performed it is convenient that before the evaporation step, the oil phase contains antiagglomerating agents, and those coformulants known by the skilled in the art to facilitate flowable formulations (e.g., clays, aluminosilicates, etc.) available in any specialized book. Another way to obtain dry microcapsules (free from solvent) is to perform a state of the art unitary operation of filtration or centrifugation.

It is also possible that a further oil soluble compound, more specifically, an oil-soluble active ingredient, is in the form of suspension in the oil phase. Then the drying step or the filtration (or ultrafiltration) step will render a mixture of flowable microcapsules and oil soluble ingredient in solid form. To make this mixture usable, any state of the art process for facilitating the flowability may be used. A particular embodiment included in this claim is the formation of water dispersable granules starting from the solution of microcapsules. The known methods of spray-drying of normal phase microcapsules may be used for this purpose. Must be noted that the prior art does not describe at all either the need of agricultural water dispersable granules (problem not addressed) with reverse phased microcapsules or the way how to obtain them. It is clear that a controlled release of water soluble agrochemicals has its advantages, the same as all already claimed for normal microencapsulation.

It is inventive to obtain water dispersible granules from RPµ since the different situation of the oil and water phase affect extremely how the coformulants to obtain the WDG must be selected (mainly oil-soluble in this case). Surpressively we have found that the evaporation of a solvent instead of the traditional evaporation of water does not affect the possible use of the microcapsules of claim 1 in the form of water dispersable granules.

§6 The microcapsules of claim 1, although in principle they are obtained with an oil phase as external and continuous phase, can be dried and then redispersed again in a watery media (optionally with other hydrophyllic solvents, e.g., ethanol for medical applications), with the aid of necessary surface active compounds. The process to obtain this formulation would be, for example: 1) spray dry or evaporating the resulting microcapsule's dispersion in oil according the claimed method 2) redisperse this microcapsules in a water media with the necessary coformulants, at least with surface active compounds, This surface active compounds can be, for example, a mixture of arabic gum, and soy lecithin at 15% in water, being the concentration of microcapsules at 20% (wt.-%).

A further dispersing agent is recommended, as the Dispersing Agent LFH and optionally also Atlox G-5000. Then we have water microencapsulated compound(s) dispersed in water, with the ecological advantages that this kind of formulation have (in agriculture), or the other advantages in cosmetics or pharmaceuticals that are directly consequence of avoiding any organic solvent in a formulation of the microcapsules according claim 1.

§7 This invention provides a solution to have the microcapsules surrounded by an external oil phase with the aid of necessary surface active compounds. Even if the process described below provides an oil phase surrounding (containing) the microcapsules it is possible to "substitute" this oil phase by another oil phase, by means of filtering/drying—from solvent—the microcapsules and redispersing them in another solvent. This acquires its best significant when, by needs of the process, the desired final formulation of microcapsules must have an oil phase wherein the microencapsulation reaction cannot be carried out. For example, if we would like to have a liquid amine derivative as organic unpolar solvent as a continuous phase in the final formulation, this could not be directly obtained by the process described in this invention, due to the nature of the purposively selected wall forming materials (the amine groups would react with the isocyanates immediately). Therefore it would be needed this "two-step" change of continuous oil phase.

§8 The process proposed to arrive to the desired microcapsules containing a water phase and water soluble and/or water dispersible compound(s) therein consist in the steps:

1) providing an aqueous phase containing at least one compound—active ingredient—to be microencapsulated, preferably at least one water soluble or dispersable compound, preferably an agrochemical, optionally at least a water soluble surface active ingredient; optionally water soluble surfactant(s), antioxidants, UV-protectors, emetics, clays; and in the case that the active ingredient(s) is(are) to be totally or partially dispersed in water, a water dispersing agent, eventually milling it(them) in an aliquot of the water phase to disperse such active ingredient(s), provided that if there is any solid a.i. in the water phase, the affinity for the water phase must be higher than the affinity for the oil phase 2)

2) providing an oil phase containing at least an unpolar solvent substantially insoluble in water, preferably a naphtha solvent or aliphatic or aromatic petroleum distillate, vegetable or mineral oils; the wall forming materials selected from the group: glycoluril resins, preferably fully butoxylated glycoluril resin, aliphatic isocyanate resins, preferably of the chemical type Cymel® 3741, and preferably combined with TMXDI; and at least oil soluble surface active ingredient(s), preferably, and a catalyst of the type dibutyltinlauralte an optionally a proton transfer catalyst (but necessarily if no catalyst is added in step 3).

3) emulsifying the aqueous phase into the oil phase, at a temperature of 40 to 60° C. this step initiates the in situ polymerization reaction of the wall forming materials onto the water droplets, optionally adding oil soluble catalyst when the polymerization reaction has already begun—preferably DBU or any similar azapolycyclo catalyst—, about 5-30 minutes after the addition of the water phase to the oil phase (but necessarily if no catalyst is added in step 2)

4) raising the temperature for the curing of the microcapsules to 60-100° C.

5) Adding to the resulting dispersion of microcapsules in oil further coformulants soluble or dispersible in oil surface active coformulants, optionally clays, aluminosilicates, viscosity modifiers, antioxidants, UV-protectors, wetting agents, perfumes, emetics; optionally this addition is made dissolving previously these coformulants into the same unpolar solvent(s)

It is meant that it can be microencapsulated one or several compounds. When referred to "compounds" we refer to the a.i. of the microencapsulated formulation.

It is excluded from the scope of the invention such combination of a.i., coformulants, solvents, wall forming materials that are chemically incompatible. This is easy to know by the skilled chemist based on the chemical characteristics of the compounds, and in the case of doubt a simple error and trial step will clarify if the invention may be applied for a determined combination of a.i. and coformulants.

In the claim that reflects this process, the active ingredient(s) [a.i.] is(are) meant to be inside the microcapsules.

In the step 1) it is contemplated the possibility that:
a) the a.i. is fully water soluble at the concentration used
b) the a.i. is water soluble, but the concentration in the water phase is over the solubility limit, then part of the a.i. would be precipitated
c) the a.i. in insoluble in water In the cases b) and c), in order that the invention is workable, such a.i. must be able to be dispersed in the water phase. For that, the common catalogs of dispersing agents' distributors provide enough information to choose the right dispersant for each a.i. It is also possible to perform a milling step in water containing the a.i. until reaching a determined particle size, preferable below 100 µm, this pre-step being done preferably with the aid of a dispersant chosen according common knowledge for the formulation chemist.

In order that during the emulsification step the solid particles are not "expelled out" of the water phase, it is needed that the a.i. is at the same time insoluble in the oil phase chosen for step 2), or at least and more importantly, that the affinity for such oil phase is lower to that of the water phase. Obviously, the skilled in the art will chose the right oil phase in which such solid particles are not soluble in it. This information is customarily provided in the material data sheets of the a.i., or in general information on the product or catalogs or in the Pesticide Manual (BCPC, ISBN 1-901396-34-7), Merck Index, etc. In such documents it can be seen in which solvents the a.i. is insoluble. It is not to expect that the coformulants would provoke a drastic change on the solubility of the chosen a.i. that would deviate from the information provided in such catalogs/publications. In the few cases that is needed, a trial and error test of partitioning a small quantity of the a.i. in between the two phases (e.g. in a separatory funnel of 250 mL), and then visualizing where the solid particles tend to be or its dissolution behavior under shaking. For extremely accurate results, a usual GC or HPLC chromatographic analysis of each phase would be sufficient to quantify the solubility.

There are hundreds of possible coformulants for the water phase that may be used according our invention. The selection of them is, however, obvious. A UV-labile water soluble compound would need the presence of a UV-protector, always choosing as first choice those coformulants that are water soluble. An easily oxidable pharmaceutical a.i. would need (maybe) the presence of an antioxidant, e.g., ascorbic acid. A formulation containing microbiologically degradable compounds may need the presence of a water soluble microbiological agent (e.g. nipagin, nipasol). An a.i. that is highly toxic may be convenient to be microencapsulated with an emetic (e.g., in the case of diquat or paraquat would be reasonable to use an emetic).

The oil phase of 2) comprises substantially (generally > 50% in wt.-%) an unpolar solvent, it is said, immiscible with water. The selection of the oil phase is generally done in the view of:
  approved solvents for each purpose (e.g., for agricultural formulations, the unpolar solvent must be selected from the corresponding list of approved solvents for agrochemicals; for pharmaceutical formulations, those solvents approved respectively, etc).
  the solubility of the a.i. to be microencapsulated, and eventually secondary a.i. in the water phase (e.g. synergistical raticide) (e.g., the a.i. must be not soluble of very low soluble in the unpolar solvent chosen, normally with a solubility lower than that in water)
  the suitability for the microencapsulation step (e.g., not reactive with isocyanates or glycoluril resins)
  the solubility of a oil soluble a.i. that is pretended to be placed in the oil phase, to form a formulation with a.i. both in the microencapsulated water phase and in the oil phase (same criteria of selection as mentioned above applies, namely, catalogs, handbooks, MSDSs, etc)

We will refer for common sources of information for the selection of the appropriate unpolar solvent: e.g., lists of approved unpolar (organic) solvents for agriculture in the case of the application of the invention in this area.

Features in this claim 8 referring to the wall forming materials have been already being discussed above. We insist in that the application of glycoluril resins for formation of microcapsules in reverse phase have never been disclosed, also has not been disclosed the purposive selection of TMXDI in the field of RPµ. While this compound is very well known in NPµ, no application of it in the RPµ has been reported, or at least, the better results obtained with it in the RPµ over other isocyanates. Worthy to note the abovementioned general knowledge book in what it is stated that the wall forming materials for RPµ must be in the water phase, being our solution then against the prior art beliefs.

The step 3) consists in the emulsification, with the novel and suppressive feature that, in the best form to reproduce the invention, we use both a non-nitrogenated proton transfer catalyst and a polycyclo-polyaza catalyst that is added in watery solution but—distinctive feature—only after the emulsification and polymerization reaction has begun. This avoids any side reaction in the water phase prior to the reaction itself. Prior art shows always that the catalyst is present in the water phase as part of it, and it is nowhere suggested that the addition of the water-soluble catalysts can be done on the reactor itself. Moreover, we show how this cycloaza catalysts are very appropriate for RPµ. It is absolutely not direct the conclusion that if this catalyst type works for NPµ, it will work in RPµ, lesser adding it when we do it.

Once the microcapsules are formed—step 4)—, the curing (hardening and fixation of the wall) is performed by raising the temperature. For those a.i. thermally label is preferably a longer curing period (e.g., at 45-55° C.) during several hours (e.g., 6 h) than a preferred temperature of 70° C. for 1 h.

The step 5) is an optional step to accomplish a "ready to use" formulation right on the reactor where the microencapsulation has taken place. The quantity and type of coformulants to add will depend strongly on the final use of the formulation, and the area of use (cosmetic, agricultural, nutraceutical, etc). The same common sense and sources of information for the choice of coformulants mentioned above for the water phase applies here. As far as preferably the coformulants added at this step are oil soluble, it is sometimes better to take a certain amount of the unpolar solvent used in 2), then mix the coformulants in a fast way by high shear stress, and then add this portion to the total (this way we do not destroy microcapsules in the mixing of coformulants). If time is not limiting, the coformulants may be added just by gently anchor stirring (e.g., 10-40 rpm).

Coformulants that are surface-active compounds appropriate for our invention can be selected from the following:

Dispersing Agents

Tristyrylphenol ethoxylate, TEA of phosphated tristyrylphenol ethoxylate, EO/PO block copolymers, phosphated, sodium fatty acid methyl tauride, sodium alkyl naphthalene sulfonate, sodium condensed naphthalene sulfonate, polymerisation product of PO/EO, sodium salt of a cresolformaldehyde condensation product of a sodium salt Wetting Agents
isotridecyl alcohol ethoxylate, sodium alkyl naphthalene sulphonate, sodium lauryl sulphate, sodium fatty acid methyl tauride, sodium dioctylsulfosuccinate Defoamers
Silicone based defoamers, fluorinated defoamers Regarding the availability of the coformulants, we present a selected list of commercial products (Uniquema, ICI) able to be used in particular embodiments of the present invention:

| | |
|---|---|
| Atplus 124 | alcohol alcoxylate blend |
| Atplus LSA9103 | alcoxylated linear synthetic alcohol |
| Atplus261 | athoxylated alcohol blend |
| Lubrol 17A17 | POE-(17)-oleyl alcohol |
| Synperonic 91/8 | POE-(8)-synthetic primary C9/C11 alcohol |
| Synperonic A2 | POE-(2)-synthetic primary C13/C15 alcohol |
| Atplus 121 | alkylaryl sulphonate in solvent |
| Atplus 469 | alkyl polysaccharide blend |
| Atplus APS b9101 | branched alkyl polysaccharide |
| Atplus 505 | fatty amine ethoxylate |
| Atlas G-3780A | POE-(20)-fatty amine ethoxylate |
| Synprolam 35X15 | POE-(15)-C13-C15 synthetic amine |
| Atlox 3300B | isopropyl alkylaryl asulphonate |
| Atlox 4838B | calcium alkylaryl sulphonate in ethyl hexanol |
| Atlox 5405B | mixture of anionic and nonionic surfactants |
| Synperonic T/304 | alcoxylated ethylene diamine (Mw 1650) |
| Tween 20 | POE-(20)-sorbitan monolaurate |
| Tween 85 | POE-(20)-sorbitan trioleate |
| Atlas G-1087 | POE sorbitol Oleate |
| SCS 2662 | methyloleate/surfactant (83/17) |
| SCS 2941 | methylated rapeseed oil/surfactant (83/17) |
| Atplus 411F | mineral oil/surfactant |
| Atplus MBA 1303 | mono branched fatty alcohol alcoxylate |
| Atplus MBA 13/10 | POE (10) monobranched fatty alcohol |
| Atlox 4914 | modified polyester |
| Atlox 4885 | sorbitan trioleate |
| Atplus UCL 1003 | Atplus 13/15 on urea |
| SCS 6076 MBA | vegetable oil/surfactant (83/17) |
| Atlox 3387BM | mixture of anionic and nonanionic surfactants |
| Atlox 3400B | mixture of anionic and nonanionic surfactants |
| Atlox 3404FB | calcium alkylaryl sulfphonate, nonionics blend |
| Atlox 4852B | alkyl aryl sulphonate with POE ether (contains NPE) |
| Synperonic PE/F108 | Ethoxylated polypropylene oxide (Mw 14000) |
| Atlox 1285 | POE-(54)-castor oil |
| Atlox CSO 5650 | POE castor oil |
| Atlas G-1300 | POE-(200)-castor oil |
| Sunaptol CA350 | POE-(35)-castor oil |
| Ukanil 2507 | POE-(32)-castor oil |
| Atlox 8916TF | POE-sorbtan esters of mixed fatty and resin acids |
| Tween 80 | POE-(20)-sorbitan monooleate |
| Atlox 1045A | POE sorbitol oleate laurate |
| Atlas G-1049 | POE sorbitol septaisostearate |
| Arlatone T | POE-(40)-sorbitol septaoleate |
| Atlace 186 | glycerol mono and dioleate and propylene glycol |
| Atlox 4848 | POE alkyl (C12/C13) methyl ether |
| Atlox 4849 | POE nonyl phenol methyl ether |
| Atlox MBA 1306 | mono branched fatty alcohol alcoxylate |
| Atlox MBA 13/8 | POE-(8)-monobranched fatty alcohol |
| PEG 200 | polyethylene |
| Atlox 4912 | nonionic block copolymer |
| Atlox 4913 | acrylic copolymer solution |
| Atlox LP1 | Polymeric disperant |
| Atlox LP6 | Polymeric disperant in high boiling petroleum fraction |
| Hypermer B261 | nonionic block copolymer |
| SCS 4447 | branched carboxylic copolymer partial ester |
| SCS 4477 | polymeric disperant (previous trademark: Atlox LP5) |
| Span 80 | sorbitan monooleate |
| Atplus 300F | sorbitan ester blend (contains NPE) |
| Atplus 309F | sorbitan ester blend (NPE free version of Atplus 300F) |

The glycolurils of first choice as wall forming materials are (CYTEC Ind.):
Highly alkylated butylated Glycolurils (Cymel 1170)
Highly alkylated Mixed alcohols Glycolurils (Cymel 1171)
Highly alkylated methylated Glycolurils (Powderlink 1174)
Unalkylated Glycolurils (Cymel 1172)

Particularly interesting additives for glyphosate, sulfosate or glufosinate formulations are Atplus 258, Altplus 411F, Atlox 70145, SCS 2397, regarding their biological activity.

Note that the relevance of the list is to achieve a perfect agriculturally functional formulation: The long list is not provided to confuse the skilled in the art, since the microcapsules either the process are affected significantly by the use of one or other coformulant: what is affected is the final performance in the field. As it would be unrealistic to provide the perfect formulation for each type of formulation containing RPμ, and for each active ingredient where our invention may be applied, we provide for the purposes of clarity and enabling the invention a limited but comprehensive list of workable coformulants.

Although the present invention offers various possibilities regarding the solvents to use for the oil phase, these does not represent problem of selection, since the specialized scientific papers or even worldwide reference handbooks describe the solubility of a.i. in different solvents, thus offering a fast answer to the question (if not immediate, pointing out to the solution) of which is the most appropriate solvent for the oil phase.

§9 In the mentioned process may exist compounds or surfactants dispersed in the water, provided that they have no affinity to the determined oil phase chosen in step 2) of claim 8, namely, substantially insoluble in the oil phase.

§10-§14 Support for claim 10-14 have been elsewhere in the description already been given §15 A more restricted process is a process for producing a formulated composition containing microcapsules that encapsulate at least a water soluble or water dispersible biologically active compound within a wall made of the reaction of a least a glycoluril resin and an isocyanate resin, and optionally TMXDI, which process comprises:

1) providing an aqueous phase containing at least on compound to be microencapsulated, preferably at least one water soluble agrochemical, optionally at least a water soluble surface active ingredient
2) providing an oil phase containing at least an unpolar solvent substantially insoluble in water, the wall forming materials selected from the group: glycoluril resins, preferably fully butoxylated glycoluril resin, aliphatic isocyanate resins, preferably of the chemical type Cymel® 3741, and preferably combined with TMXDI; and at least oil soluble surface active ingredient(s), preferably of the type LP-6 and/or Atlox® 4914 and optionally a non-nitrogenated proton transfer catalyst (but necessarily if no catalyst is added in step 3).
3) emulsifying the aqueous phase into the oil phase, at a temperature of 40 to 60° C. this step initiates the in situ polymerization reaction of the wall forming materials onto the water droplets, optionally adding an oil soluble aza catalyst of the type DBU when the polymerization reaction has already begun, about 5-30 minutes after the addition of the water phase to the oil phase (but necessarily if no catalyst is added in step 2)
4) raising the temperature for the curing of the microcapsules to 60-100° C.

Adding the necessary coformulants to form a functionally acceptable agricultural formulation preferably at least two surface active materials, optionally at least an alumiosilicate-based material or material providing the same functionality of it, and all these coformulants optionally being in organic unpolar solvent(s), most preferably the same unpolar solvent(s) present in the oil phase of step 2).

§17 Preferred sulfonylureas to be included in any oil phase where the RPμ are present, are: Amidosulfuron, Bensulfuron-methyl, Chlorimuron, Chlorsulfuron, Cinosulfuron, Cyclosulfamuron, Ethametsulfuron-methyl, Ethoxysulfuron, Flazasulfuron, Flupyrsulfuron-methyl, Foramsulfuron, Halosulfuron-methyl, Imazosulfuron, Iodosulfuron-methyl, Mesosulfuron, Metsulfuron-methyl, Nicosulfuron, Oxasulfuron, Primisulfuron-methyl, Prosulfuron, Pyrazosulfuron-methyl, Rimsulfuron, Sulfosulfuron, Thifensulfuron-methyl, Triasulfuron, Tribenuron-methyl, Trifloxysulfuron, Triflusulfuron-methyl, Tritosulfuron, noting that any derivative of these molecules is also included in this claim, optionally alkyl derivatives, dealkylated derivatives and/or salts thereof. This refers to the typical variations: thifensulfuron-ethyl<→thifensulfuron, etc. When the sulfonylureas are in a salt form, and the solubility in the desired oil solvent is not enough to reach a biological effect in the field, then it is preferred that such sulfonylurea derivative is added in the water phase and microencapsulated in RPμ.

§18 The process of mixing a SC with a CS of RPμ is explained in the Example 7. We also claim a formulated agrochemical composition according claim 8 or 15 wherein, apart from a water soluble or water dispersible microencapsulated agrochemical, it is present at least a water soluble compound or oil-soluble compound dispersed into the oil phase, preferably by milling such compound(s) in a separated aliquot of the oil phase—but containing no microcapsules—and then mixing the milled compound(s) together with this aliquot to the microencapsulated fraction §19-20 Formulated agrochemical compositions of the type CS, CX, WDG, ZC, CS-EC, OD (oil dispersion) according the invention may have at least a water soluble microencapsulated agrochemical selected from the group: glyphosate, glufosinate, glufosinate, paraquat, diquat, chlormequat, 2,4-D,—both in any form, preferably in salt form—an the oil phase contains diflufenican or at least an aryoxyphenoxypropionate, preferably Quizalofop-P-ethyl or propaquizafop-ethyl or fenoxaprop-P-ethyl. Also formulations of sulfonylureas in the claimed types [CS, CX, WDG, ZC, CS-EC, OD] are particularly preferred, in so far RPμ are present, and of this, nicosulfuron is of great interest and proven to be at least 20% times more stable to hydrolysis than current commercial formulations, when embodied in a CX being microencapsulated in NPμ and combined with sulfosate.

§21 "Quat" herbicides, preferably chosen from chloride or bromide-paraquat, diquat, chlormequat, are object of this invention, in so far microencapsulation offers a solution to its high toxicity, combined with an oil phase contains a sulfonylurea or sulfonamide herbicide.

§22 Glufosinate and lactofen is a very effective combination proven to act synergistically in our greenhouse tests (results not shown).

§23 A formulated agrochemical composition of the type water dispersable granules containing microcapsules according claim 1 or 2 is of high interest, since this solid flowable compositions are very preferred by the farmers and reduce transport costs of solvents. A picture of this type of formulation is shown in FIG. 3.

§24 A formulated agrochemical composition of the type ZC (suspension concentrate plus capsule suspension) containing microcapsules according claim 1 or 2 is shown in FIG. 4.

§25 A formulated agrochemical composition consisting of a combination of an emulsion concentrate plus capsule suspension, containing microcapsules according claim 1 or 2 is one of the preferred embodiments for its easiness of preparation with very interchangeable Adjustment Mixtures (see Example 1).

§26-35 This invention provides for the first time an enabling disclosure of agrochemical formulations characterized in that they contain:

a) Reverse phase microcapsules containing a watery core wherein at least water soluble active ingredient is present b) Normal phase microcapsules containing a oily core wherein at least an oily soluble active ingredient is present Is described herein for the first time. Since the object of this invention is to find new ways to use in agriculture water-soluble agrochemicals, we do not restrict the claim to the RPμ explicitly shown in claim 1 or in process 8. Rather, this revolutionary type of formulation may be used with any kind of RPμ—present or future—, in so far the size and performance is acceptable. Of course, as preferred embodiment of this formulation is that where our RPμ are used, and also where the NPμ wall is created as in Example 5, with mixed polyurea-glycoluril wall. Formulations of mixed microcapsules are those having as continuous phase water, oil, WDG, SC-RPμ-NPμ, EC-RPμ-NPμ, RPμ-NPμ in the form of oil dispersion—wherein in the oil dispersion is present a further active ingredient—, or equally, as emulsion concentrate where in the oil it is present a further active ingredient.

§35 The mixed NPμ+RPμ are specially suitable for combining different classes of agrochemicals, namely, the a.i. are combined to have different biological effects, preferably the combination of: fungicides+herbicides, fungicides+insecticides, insecticides+herbicides, insecticides+plant growth regulators, insecticides+semiochemicals, provided that in the case of existing the two different microcapsules according claim 26 a) and b), each type of microcapsule contains a biologically active different material (in the sense of the target living organisms to control).

Particular embodiments of the present invention are: reverse phase microcapsules containing glyphosate isopropylammonium dispersed in an oil or water phase; reverse phase microcapsules containing glyphosate isopropylammonium trimesium dispersed in an oil or water phase: reverse phase microcapsules containing glyphosate ammonium dispersed in an oil or water phase: reverse phase microcapsules containing sulphosate ammonium dispersed in an oil or water phase; reverse phase microcapsules containing glufosinate ammonium dispersed in an oil or water phase; reverse phase microcapsules containing 2,4-D dispersed in an oil or water phase; reverse phase microcapsules containing MCPP-sodium dispersed in an oil or water phase; reverse phase microcapsules containing MCPA-sodium dispersed in an oil or water phase; reverse phase microcapsules containing diquat bromide (or bromide) dispersed in an oil or water phase; reverse phase microcapsules containing paraquat chloride (or bromide) dispersed in an oil or water phase; reverse phase microcapsules containing glyphosate combined with an oil phase containing nicosulfuron; both as oil dispersion or as water dispersable granules (WDG) after spray drying of such oil dispersion; reverse phase microcapsules containing glyphosate combined with an oil phase containing thifensulfuron-methyl; both as oil dispersion or as water dispersable granules (WDG) after spray drying of such oil dispersion; reverse phase microcapsules containing glyphosate combined with an oil phase containing metsulfuron-methyl; both as oil dispersion or as water dispersable granules (WDG) after spray drying of such oil dispersion; reverse phase microcapsules containing glyphosate combined with an oil phase containing rimsulfuron; both as oil dispersion or as water dispersable granules (WDG) after spray drying of such oil dispersion; reverse phase microcapsules containing glyphosate combined with an oil phase containing tribenuron-methyl; both as oil dispersion or as water dispersable granules (WDG) after spray drying of such oil dispersion; reverse phase microcapsules containing glyphosate combined with an oil phase containing foramsulfuron; both as oil dispersion or as water dispersable granules (WDG) after spray drying of such oil dispersion; reverse phase microcapsules containing glyphosate combined with an oil phase containing iodosulfuron; both as oil dispersion or as water dispersable granules (WDG) after spray drying of such oil dispersion; reverse phase microcapsules containing glyphosate combined with an oil phase containing chlorsulfuron; both as oil dispersion or as water dispersable granules (WDG) after spray drying of such oil dispersion; reverse phase microcapsules containing glyphosate combined with an oil phase containing chlorimuron or mesosulfuron; both as oil dispersion or as water dispersable granules (WDG) after spray drying of such oil dispersion; reverse phase microcapsules containing glyphosate combined with an oil phase containing triflusulfuron; both as oil dispersion or as water dispersable granules (WDG) after spray drying of such oil dispersion; reverse phase microcapsules containing glyphosate combined with an oil phase containing quizalofop-P-ethyl; both as oil dispersion or as water dispersable granules (WDG) after spray drying of such oil dispersion; reverse phase microcapsules containing glyphosate combined with an oil phase containing propaquizafop-ethyl; both as oil dispersion or as water dispersable granules (WDG) after spray drying of such oil dispersion; reverse phase microcapsules containing glyphosate combined with an oil phase containing fenoxaprop; both as oil dispersion or as water dispersable granules (WDG) after spray drying of such oil dispersion; reverse phase microcapsules containing glufosinate and/or sulfosate combined with an oil phase containing nicosulfuron; reverse phase microcapsules containing glufosinate and/or sulfosate combined with an oil phase containing thifensulfuron-methyl; reverse phase microcapsules containing glufosinate and/or sulfosate combined with an oil phase containing metsulfuron-methyl; reverse phase microcapsules containing glufosinate and/or sulfosate combined with an oil phase containing rimsulfuron; reverse phase microcapsules containing glufosinate and/or sulfosate combined with an oil phase containing tribenuron-methyl; reverse phase microcapsules containing glufosinate and/or sulfosate combined with an oil phase containing triflusulfuron; reverse phase microcapsules containing glyphosate isopropylammonium combined with an oil phase containing diflufenican; reverse phase microcapsules containing glyphosate isopropylammonium (or glufosinate ammonium or sulfosate ammonium), combined with an oil phase containing lactofen; reverse phase microcapsules containing glyphosate isopropylammonium (or glufosinate ammonium or sulfosate ammonium) combined with an oil phase containing flufenacet; reverse phase microcapsules containing glyphosate isopropylammonium (or glufosinate ammonium or sulfosate ammonium) combined with an oil phase containing fluoroxypyr-meptyl; reverse phase microcapsules containing glyphosate isopropylammonium or glufosinate ammonium or sulfosate ammonium, combined with an oil phase containing isoxaflutole; reverse phase microcapsules containing glyphosate isopropylammonium or glufosinate ammonium or sulfosate ammonium, combined with an oil phase containing deltamethrin (for control of weeds and insects); reverse phase microcapsules containing glyphosate isopropylammonium or glufosinate ammonium or sulfosate ammonium, combined with an oil phase containing lambda-cyhalothrin (for control of weeds and insects); reverse phase microcapsules containing glyphosate isopropylammonium or glufosinate ammonium or sulfosate ammonium, combined with an oil phase containing alfa-cypermethrin (for control of weeds and insects); reverse phase microcapsules containing glyphosate isopropylammonium or glufosinate ammonium or sulfosate ammonium, combined with an oil phase containing gamma-cyhalothrin (for control of weeds and insects); reverse phase microcapsules containing glyphosate isopropylammonium or glufosinate ammonium or sulfosate ammonium, combined with an oil phase containing imidacloprid (for control of weeds and insects): reverse phase microcapsules containing glyphosate isopropylammonium or glufosinate ammonium or sulfosate ammonium, combined with an oil phase containing spirodiclofen (for control of weeds and mites); reverse phase microcapsules containing glyphosate isopropylammonium or glufosinate ammonium or sulfosate ammonium, combined with an oil phase containing tebuconazole (for control of weeds and fungi); reverse phase microcapsules containing glyphosate isopropylammonium or glufosinate ammonium or sulfosate ammonium, combined with an oil phase containing fosetyl-Al (for control of weeds and fungi); reverse phase microcapsules containing glyphosate isopropylammonium or glufosinate ammonium or sulfosate ammonium, combined with an oil phase containing trifloxystrobin (for control of weeds and fungi); reverse phase microcapsules containing glyphosate isopropylammonium combined with normal phase microcapsules (either in oil or water continuous phase) containing tribenuron-methyl; reverse phase microcapsules containing glyphosate isopropylammonium combined with normal phase microcapsules (either in oil or water continuous phase) containing triadimenol; reverse phase microcapsules containing glyphosate isopropylammonium combined with normal phase microcapsules (either in oil or water continuous phase) containing clomazone; reverse phase microcapsules containing glufosinate ammonium combined with normal phase microcapsules (either in oil or water continuous phase) containing fluorochloridone; mixtures of reverse phase microcapsules containing glyphosate, gluphosinate, sulfosate, paraquat, diquat, chlormequat or 2,4-D and normal phase microcapsules containing: sulfonylureas, "fop" herbicides—e.g., Quizalofop-P-ethyl, fenoxaprop, propaquizafop—, clomazone, triazol fungicides—e.g., propiconazole, tebuconazole, triadimenol—, pyrethroids, fluorochloridone, lactofen, diflufenican, flufenacet, azoxystrobins, spinosad, trimedlure, benzoylureas—e.g., hexaflumuron, novaluron, triflumuron, lufenuron—, juvenile hormones, chitin synthesis inhibitors—e.g. ciromazine—, semiochemicals, Metazachlor, butachlor, alachlor, organophosphates, phosphtionates, chlorinated or fluorinated persistent insecticides—e.g., DDT, 666—;

all in a concentration (both in the formulation itself and in the spray tank) that yields the recommended values of a.i. per Hectare when applied in the field, preferably at the same concentrations as the ones used in state of the art non-microencapsulated or microencapsulated commercial products containing such a.i.

The reader will immediately recognize that the change of a certain salt form of the water soluble a.i. is irrelevant: e.g., the use of glyphosate isopropylammonium can be easily replaced by glyphosate ammonium, or any other salt or organic derivative—in so far the solubility properties are not tremendously changed—e.g., for a maximum solubility of 40% in water a change to a solubility of 1%—and the concentration adjusted to match the same content in free glyphosate acid form. This also applies similarly to other oil soluble a.i., e.g.: Quizalofop-P-ethyl can be easily replaced by Quizalofop-ethyl (a racemic mixture), metsulfuron-methyl can be replaced by metsulfuron, propaquizafop-ethyl can be replaced by propaquizafop, as so on. There is nothing in this invention that prevents such elementary changes.

All this formulations have been realized, although for reasons of simplicity, only the complete details of the formulation of some of them are disclosed. However, with the examples provided, all formulations mentioned are implicitly disclosed in a fully enabling disclosure, since the only that the skilled in the art needs to do is just to replace the content in active ingredient from one to another.

The following examples show how the invention is easily embodied with surprising results regarding the easiness of the process and the stability and performance achieved by the claimed formulations.

In all examples, and also everywhere in this document, the percentages are referred to weight percent.

FIG. 1 shows the distribution of particle size of the formulation capsule suspension of oxytetracycline hydrochloride in RPµ and milled tebuconazole.

FIG. 2 shows the typical viscosity diagram of a formulation of diflufenican and RPµ glyphosate.

FIG. 3 shows water dispersable granules of RPµ.

FIG. 4 shows microcapsules of a CX formulation (RPµ+NPµ formulation).

EXAMPLE 1

A capsule suspension formulation of the water soluble herbicide glyphosate in its isopropylamine salt form (in short, G-IPA), was performed as follows (later also, a mixed formulation with the water-insoluble herbicide diflufenican).

A water phase containing the G-IPA and an oil phase were made, and warmed at 50° C., in separate vessels according to:

| Components | Parts |
| --- | --- |
| Water Phase | |
| G-IPA solution in water at 60% | 53 |
| Oil Phase | |
| TMXDI | 5 |
| Cythane ® 3174 | 0.5 |
| Cymel ® 1170 | 0.1 |
| Atlox ® 4914 | 3 |
| Atlox ® LP-6 | 3 |
| Solvesso ® 200 | 34.1 |
| Dibutyltinlaureate in gamma-butyrolactone solution (1%) | 1 |

2) The water phase is transferred (poured) slowly but continuously to the oil phase during 1 minute into the oil phase, under continuous agitation with an Ultraturrax L4 mixer for 10 minutes.

3) Before the conclusion of the 10 minute period mentioned above, and after finalization of the addition of the water phase to the oil phase, a solution in Solvesso 200 (at 10%) of {1,8-}Diazabicyclo[5.4.0]undec-7-ene [in short, DBU] is added to the emulsified solution—0.15% over total percentage—(preferably 1 minute after emulsification begins, namely, after total addition of the water phase).

4) After the period of 10 minutes, the reactor vessel is left at 60° C. and with gentle agitation (with an anchor type stirrer at 25 rpm) for a period of 2 hours (curing of microcapsules). After this period of curing, we have a Concentrated Glyphosate CS formulation [in short, C.G.-CS]. At this time we obtain microcapsules with a median size of 1.8 µm. Oil Phase 5) At this point we can choose to have a Glyphosate CS 250 g/L formulation [point 5.1)] or we can combine the microcapsules with an oil phase containing another active ingredient [point 5.2)] in the form of Emulsion Concentrate (EC) like a Mixed formulation Glyphosate 200 g/L CS and diflufenican 80 g/L EC.

5.1) Although at this moment, after the curing, the formulation is perfectly microencapsulated and stable, for the purposes of using the formulation as a ready to use agrochemical formulation, an Adjustment Mixture A [in short, A.F.-A] is added to the capsule suspension resulting from point 4) [the C.G.-CS] in a ratio A.F.-A/C.G.-CS of 20/80.

| Components Adjustment Mixture A | Parts (making up to 20%) |
| --- | --- |
| Atlox ® G-5000 | 0.13 |
| Dispersing Agent LFH | 10.00 |
| Atlox MBA 13/8 | 3.50 |
| Attagel 50 (solution at 20% in Solvesso ® 200) | 2.00 |
| Solvesso ® 200 | 4.37 |

After the mixing of A.F.-A with the C.G.-CS we have a ready to use Capsule Suspension of Glyphosate at 250 g/L.

The physicochemical characteristics show, for the final product, that the median particle size, determined by a laser Mastersizer equipment, is of 9.5 µm, with a viscosity nu at $tau_{10}$ of 248.0 cP and a yield stress of tau0=2.47 Pa at gamma=0, with a density of 1.1242 g/L, and with a conductance of 0.001 S (meaning that the water phase has effectively retained inside the microcapsules).

5.2) Alternatively the C.G.-CS may be mixed with the following Adjustment Mixture B [A.F.-B] {instead of using the A.F.-A}, in order to obtain a synergistic herbicidal mixture containing glyphosate CS and diflufenican EC (emulsion concentrate):

| Components Adjustment Mixture B | Parts |
| --- | --- |
| Atlox ® G-5000 | 0.13 |
| Dispersing Agent LFH | 10.00 |
| Atlox MBA 13/8 | 3.50 |
| Attagel 50 (solution at 20%) | 2.00 |
| Solvesso ® 200 | 13.20 |
| Diflufenican | 8.06 |

After the mixing of A.F.-B with the C.G.-CS at a ratio 37:63 we have a ready to use Capsule Suspension of Glyphosate at 200 g/L and Emulsion Concentrate of diflufenican at 80 g/L.

The physicochemical characteristics show, for the final product, that the median particle size, determined by a laser Mastersizer equipment, is of 14.3 µm, with a viscosity nu at $tau_{10}$ of 40.9 cP and a yield stress of tau0=1.38 Pa at gamma=0, with a density of 1.0971 g/L, and with a conductance below the limits of detection (meaning that the water phase has been effectively retained inside the microcapsules). Storage Stability Tests.

Both formulations were submitted to accelerated heat stability tests (at 54° C. for 2 weeks). None of the two formulations showed any water release from the microcapsules, either water/oil separation or emulsion.

Microscopic observation of the microcapsules showed a complete integrity. Also, presence of unencapsulated material—water soluble a.i.—was below 0.1%.

The chemical degradation of glyphosate and diflufenican was not statistically significant (fresh samples of both formulations 5.1) and 5.2) compared with aged samples did not presented differences in the Student's t-test, either with pure analytical standard solutions at the same concentration of the a.i.). These tests were performed with HPLC and standard methods of analysis under Good Laboratory Practice conditions.

EXAMPLE 2

RPμ High Loaded Formulation of Glyphosate Ammonium+EC Halosulfuron

A high loaded formulation (E2.1) of glyphosate ammonium together with the sulfonylurea herbicide halosulfuron, was prepared according the present invention, and compared with other two prior art methods of microencapsulation.

The composition is identical to Example 1 but replacing:

in the water phase: glyphosate isopropylammonium by glyphosate ammonium, and increasing its content to 65 parts (the rest oil phase remaining with the original parts).

in the oil phase: the content of diflufenican wholly by halosulfuron and that the ratio A.F.-A/C.G.-CS instead of being 22.5/77.5 is now 10/90.

The formulation showed perfectly stable microcapsules (mean diameter=1.5 μm) at 54° C. for two weeks, with 0.05% degradation of glyphosate and 5.12% degradation of halosulfuron. The halosulfuron oil concentrate (E2.2) showed a degradation of 4.82%, meaning that no increased degradation of halosulfuron was due to the process or the mixed formulation.

EXAMPLE 3

RPμ+EC Mixed Formulation of 2,4-D Sodium and Lactofen

A formulation (E3.1) of RPμ of 2,4-D sodium plus lactofen (E3.2) was made, to yield an emulsifiable concentrate containing microcapsules of 2,4-D sodium and solubilized lactofen.

The composition followed that explained in Example 1, where the glyphosate was substituted by 2,4-D (20% in water) and the diflufenican was substituted by lactofen (E3.3).

An Adjustment Mixture AM-EC, in order to create an emulsion concentrate of the formed 2,4-D+lactofen formulation was used, consisting in castor oil 20 mols ethoxylated: calcium dodecylbenzenesulfonate emulsifier (Calsogen CA): Genapol LA at the ratio 50:10:40. This AM-EC was added (200 g) to the E3.3. This CS-EC formulation (E3.4) was emulsified in water at a concentration of 5% of the formulation, showing no oil and cream separation at time 30 minutes, and 1 ml cream at 2 hours.

EXAMPLE 4

WDG-RPμ Microcapsules of Sulfosate Ammonium

A formulation according Example E1.1, using sulfosate ammonium (20% in water) as a.i. instead of glyphosate was made. At the end of the microencapsulation, a 10% (with respect total weight of formed E1.1) of sodium dioctylsulfosuccinate wetter was added and also 1% of sodium cresolformaldehyde condensation dispersant.

To this amount, an Adjustment Mixture AM-DRPμ for allowing the spray dry process was used, consisting in 48% of cyclodextrin, 2% of Arbocel™, 25% CMC (carboxymethylcellulose) and 25% dextrin. 30% over the 1000 g (300 g) of this mixture was added directly to the spray chamber, in order the oil is adsorbed in such material. The addition of further AM-DRPμ was done as needed (in this process only one batch was made, and no further addition of adsorbing materials was needed, however, at industrial scale, the retirement of already flowable microcapsules may need further additions of AM-DRPμ, in the conventional way for the skilled in spray drying technical would do for similar processes). After spray drying at a product temperature of 50° C., it was obtained a flowable powder of dispersable microcapsules of sulfosate ammonium (water dispersable granules). The wet sieving residue calculated with a sieve of 250 μm was 0.85%, having a dispersibility of 85% and a suspensibility of 92%.

EXAMPLE 5

CS2 (Mixed Formulation RPμ and NPμ) of Fluorochloridone and Acifluorfen-Sodium

A formulation of NPμ (E5.1) fluorochloridone was made according the following formula:

|  | In parts |
|---|---|
| Organic Phase: | |
| Flurochloridone (50%) in Solvesso ™ 150 | 500 |
| Benzene, 1,3-Bis(1-isocyanate-1-methylethyl)-diisocyanate (TMXDI) | 10 |
| Diphenylmethane-4,4'-diisocyanate (PMDI) | 18 |
| Dibutyltin laurate | 0.03 |
| Tetraethoxymetyl acetylene carbamide | 4 |
| Gamma-butyrolactone | 3 |
| Water Phase: | |
| Water (added independently from the other solutions) | 232 |
| 10% water solution of xanthan gum | 20 |
| 20% water solution of PVP-30 | 10 |
| 35% water solution of Arabic gum | 50 |
| LignoGAT ™ | 40 |
| Antimussol ™ 4459 | 0.25 |
| Citric Acid | 0.14 |
| Reax ™ 85A | 0.25 |

Being the Composition of LignoGAT™:

| Ingredients of LignoGAT ™ | wt % |
|---|---|
| Water | 72.2 |
| Celvol ™ 205 | 10 |
| Kraftsperse ™ 25M | 17.8 |
| Total | 100 |

A formulated RPμ (E5.2) of acifluorfen sodium was performed as in Example 1, substituting the glyphosate ammonium at 60% in water by acifluorfen sodium at 44% in water.

Now, in the step of mixing both types of formulations, it must be taken into account:

The addition to the water phase of the E5.2 of the oil phase of the finished E5.1, needs the presence of an emulsifier with HLB 7-14, preferably 9-10, or at least, that the total HLB of the emulsifiers would equate a value of 9-10. This is done in this example adding a castor oil ethoxylate 64 mols to the water phase of E5.2, in a 10% over total weight of E5.2.

The emulsification is preferably made oil in water, namely the RPμ added to the NPμ. A ratio of RPμ to NPμ of 40 to 60 is used in this example. Emulsification is done adding the RPμ as obtained in E5.2 to the E5.1 plus the mentioned surfactant with high HLB (over 7), under continuous agitation with anchor type stirrer (at about 100-1000 rpm)—this requiring that the configuration of the stirrer and the speed do not damage the microcapsules—.

This way we have obtained the RPμ+NPμ, but to avoid storage stability problems, it is recommended the addition of some viscosity modifiers to the water phase. In this example we use a mixture of Keltrol and Pangel at 1:1, in a total amount of 3% over total weight up to the moment of that viscosity modifier addition.

Finally, we have obtained, for the first time a CX-w formulation (combined capsule suspension of RPμ and NPμ), wherein we have acifluorfen sodium microencapsulated in a core of water, and fluorochloridone microencapsulated in a core of oil, and both types of microcapsules having a continuous phase of water surrounding them.

The mean size of the combined microcapsules was measured with a laser Mastersizer™, with a result of 2.9 μm and a percentile 90 of 5.3 μm. This represents an enormous degree of homogeneicity, and moreover, a very small size over the prior art RPμ. Emulsification properties were tested according FAO specifications showing no oil separation at 30 minutes and after 2 hours, and full reemulsification was shown after 24 hours. The formulation did not presented any phase separation after 2 weeks at 40° C.

No detection of degraded of any of the a.i. was possible (below limits of detection/analytical error). Unencapsulated material was below 0.5% for the acifluorfen sodium and below 0.01% for fluorochloridone.

In FIG. 4 a microphotograph is shown with the resulting final formulation. The RPμ are slightly bigger, and they can be differentiated from the NPμ in that the former have a reddish core and the NPμ have a greenish solid color.

It can be appreciated that the wall forming materials for the NPμ and the RPμ are chemically of the same nature (glycolurils+isocyanates) a surprising result that facilitates the logistic and handling operations in the formulation plant.

Further Processing

The resulting formulation of the CX-w was processed in order to obtain WDG of mixed microcapsules. To 1 kg of the resulting CX-w, an Adjustment Mixture AM-DRPμ for allowing the spray dry process was used, consisting in 50% of cyclodextrins, 25% sepiolite and 25% CMC (carboxymethylcellulose), 30% over the 1000 g (300 g) of this mixture was added directly to the spray chamber, in order the oil is adsorbed in such material. The addition of further AM-DRPμ was done as needed (in this process only one batch was made, and no further addition of adsorbing materials was needed, however, at industrial scale, the retirement of already flowable microcapsules may need further additions of AM-DRPμ, in the conventional way for the skilled in spray drying technical would do for similar processes). After spray drying at a product temperature of 63° C., it was obtained a flowable powder of dispersable microcapsules, namely WDG of CX microcapsules.

EXAMPLE 6

CX Formulation (Mixed NPμ and RPμ) of Ioxynil Sodium and Metsulfuron-Methyl

Microcapsules of the type RPμ were done (E6.1) according the following formula and process as in Example 1:

| E6.1 | Parts |
|---|---|
| Water Phase | |
| Ioxynil sodium solution in methylcellosolve at 60% | 15 |
| water | 20 |
| Oil Phase | |
| TDI | 1.5 |
| Cymel ® 1172 | 0.9 |
| Atlox ® 4914 | 3 |
| Atlox ® LP-1 | 3 |
| Solvesso ® 200 | 41.4 |
| Dibutyltinoleate in gamma-butyrolactone solution (1%) | 1 |

Microcapsules of the type NPμ were done according those in Example 5, but substituting the fluorochloridone by metsulfuron-methyl.

To the difference of Example 6, here it is added the NPμ to the RPμ. For this we need to proceed as above while inverting the need of the HLB of the surfactant, this time in the range 1-6, preferably about 2-3 (in any case lower than 7). A 10% presence of surfactant is enough to produce a good emulsion. Atlox® LP-6 is used in this example at 12%, before emulsification.

This time, due to the increased viscosity of Solvesso the emulsion was stable even without addition of viscosity modifier, although is recommended any viscosity modifier for the outer oil phase.

Finally, we have obtained, for the first time a CX-o formulation (combined capsule suspension of RPμ and NPμ), wherein we have ioxynil sodium, microencapsulated in a core of water, and metsulfuron microencapsulated in a core of oil, and both types of microcapsules having a continuous phase of water surrounding them.

The best advantage of this formulation is that the very sensitive to degradation sulfonylurea metsulfuron-methyl degraded only 3.1% in 2 weeks at 54° C. compared with commercial products containing it wherein a range from 10% till 34% has been observed in our lab at the same time and temperature conditions. Further, an oil suspension of metsulfuron-methyl, according Adjustment Mixture B of Example 1 (substituting diflufenican by metsulfuron-methyl) and adding 5% of urea in respect total oil suspension, showed degradation of 45% in 2 weeks at 54° C. This demonstrates undoubtfully that degradation of metsulfuron-methyl is almost completely inhibited by virtue of microencapsulating it, thus providing this invention a way to combine water soluble agrochemicals with labile sulfonylureas, very prone to degradation in water phase or even oil phase. The space constriction of the tiny microcapsules (1.1 μm mean diameter) limits the reactivity of the sulfonylureas, and the accumulation of any by-products that balance the equilibrium to the original sulfonylurea undegraded, makes this invention extremely useful for any sulfonylurea, since the degradation inhibition seen with metsulfuron-methyl, has been equally observed with tribenuron-methyl (results and process not shown) and there is no rationale into thinking that this protective effect cannot be extended to all sulfonylureas, that are quite similar in chemical structure. Moreover, the experiment of tribenuron-methyl was done with a emulsification into the water phase as in Example 6 (namely, obtaining a CX-w), meaning that the existence of an oil or a water phase outside of the microcapsule is irrelevant for what happens inside the microcapsule (logically). Unencapsulated material was below 0.1%. Emulsification properties were tested according FAO specifications showing no oil separation at 30 minutes and after 2 hours, and full reemulsification was shown after 24 hours. The formulation did not presented any phase separation after 2 weeks at 40° C.

EXAMPLE 7

ZC (=CS+SC) Formulation of a Capsule Suspension of Oxytetracycline Hydrochloride in RPμ and Milled Tebuconazole Against Fungal and Bacterial Attacks A RPμ (Capsule Suspension in reverse phase, CS) according example 1 was made—E7.1—, replacing the 60% solution of glyphosate-IPA with a 10% of oxytetracycline hydrochloride solution adjusted to pH 5 with citric acid (as needed).

A Suspension Concentrate do tebuconazole was performed with the following formula, and a customary milling process was carried out with DynoMill machines with glass-beads as milling mechanism.

Formula SC Tebuconazole E7.2:

|  | [wt-%] |
|---|---|
| Tebuconazole | 20 |
| Marcol 82 | 15.00 |
| Propylenglycol | 9.00 |
| Sapogenate T 80 | 4.00 |
| PAE 147 | 1.00 |
| Pangel | 0.18 |
| Celvol 205 | 0.75 |
| Ascorbic acid | 0.01 |
| Germall II | 0.04 |
| Keltrol | 0.18 |
| Atlas G 5000 | 1.00 |
| Atlox 4913 | 3.32 |
| Dispersing LFH | 1.00 |
| Antimussol | 0.50 |
| PVP 15 solution | 1.99 |
| Water | 42 |
| Total | 100.00 |

To the SC tebuconazole E7.2 a mixture of emulsifiers E7.3 consisting in castor oil 54 mols ethoxylated Soprophor 461: Tween 20 (ratio 10:80:10) was prepared in order to achieve a ZC formulation in continuous phase oil.

This emulsifier mixture was mixed at 20 parts per 80 parts of the SC, obtaining E7.4

Finally the desired ZC formulation was obtained by mixing under anchor stirring (100 rpm) 50 parts of E7.4 with 50 parts of E7.1

Unencapsulated material was below 0.1%.

EXAMPLE 8

Particle Size of RPμ of Trifloxysulfuron Sodium According the Chosen Wall Forming Materials

| Components (in %) | E8.1 | E8.2 | E8.3 | E8.4 | E8.5 |
|---|---|---|---|---|---|
| water phase | | | | | |
| Trifloxysulfuron sodium (10%) | 53 | 53 | 53 | 53 | 53 |
| oil phase | | | | | |
| TDI | — | — | — | 5 | 3 |
| HMDI | — | — | 5 | — | — |
| TMDI | — | 5 | — | — | — |
| TMXDI | 5 | — | — | — | 2 |
| Cythane 3174 | 0.5 | 0.5 | 0.5 | 0.5 | — |
| Cymel 1170 | 0.1 | 0.1 | 0.1 | 0.1 | — |
| Cymel 1171 | — | — | — | — | — |
| Powderlink 1174 | — | — | — | — | — |
| Cymel 1172 | — | — | — | — | — |
| DBTL (1% in solvesso) | 1 | 1 | 1 | 1 | 1 |
| DBU (10% in Solvesso 200) | 0.15 | 0.15 | 0.15 | 0.15 | 0.05 |
| p-toluensulfonic acid | — | — | 0.02 | 0.02 | 0.02 |
| Atlox 4914 | 3 | 3 | 3 | 3 | 3 |
| Atlox LP-6 | 3 | 3 | 3 | 3 | 3 |
| Solvesso 200 | 34.3 | 34.3 | 34.3 | 34.3 | 34.9 |
| Average Particle Size (μm) | 1.8 | 7.4 | 6.7 | 9.4 | 58.7 |
| Percentil 90 | 4.5 | 15.8 | 25.4 | 38.7 | 220 |

In these series of tests, it was investigated the effects of the wall forming materials in the size of the microcapsules.

The better result (most homogeneous microcapsules with the smaller diameter) was obtained by E8.1, well distant from the results of all other tests.

The smaller the diameter is, the faster is the release, that for most herbicides is highly desired, since the farmer desires to obtain controlling results as soon as possible. However, higher sizes may, in certain conditions be more interesting, since this provides a longer action, in general.

For the most common and most appreciated characteristics of the microcapsules for agriculture (small particle size) the ones that contain glycoluril resins show much better results. Of these, those combined with the isocyanate TMXDI provide the most homogeneous and sharpened distribution of sizes.

EXAMPLE 9

Formulations of RPμ with Different Wall Forming Materials and Location of Components for Microencapsulation

| E9.1 | wt % |
|---|---|
| water phase: | |
| G-IPA (60%) and 2,4-D at ratio 1:1 | 50 |
| Malic anhydrid (50%) | 1 |
| Synperonic A7 | 0.5 |
| oil phase: | |
| Cymel 350 | 10 |
| Cymel 1170 | 1 |
| Agrimer AL22 | 4 |

-continued

| E9.1 | wt % |
|---|---|
| Room* to add Adjustment Mixture A | 10 |
| solvesso 200 to 100% | 23.5 |

Average Particle size: 5.9 μm
Separation of oil/water phase after 2 weeks at 54° C.: no
Unencapsulated a.i.: 4.7%

| E9.2 | wt % |
|---|---|
| water phase: | |
| G-IPA (60%) and 2,4-D at ratio 1:1 | 50 |
| Cymel 401 | 5 |
| oil phase: | |
| Aristol A | 6 |
| Agrimer AL22 | 4 |
| Room* to add Adjustment Mixture A | 10 |
| solvesso 200 to 100% | 25 |

Average Particle size: 8.7 μm
Separation of oil/water phase after 2 weeks at 54° C.: no
Unencapsulated a.i.: 10.2%

| E9.3 | wt % |
|---|---|
| water phase: | |
| G-IPA (60%) and 2,4-D at ratio 1:1 | 50 |
| Malic anhydrid (50%) | 1 |
| Synperonic A7 | 0.5 |
| oil phase: | |
| Dynomin UI 20E | 10 |
| Agrimer AL22 | 4 |
| Cymel 1170 | 1 |
| Room* to add Adjustment Mixture A | 10 |
| solvesso 200 to 100% | 23.5 |

Average Particle size: 18.1 μm
Separation of oil/water phase after 2 weeks at 54° C.: no
Unencapsulated a.i.: 3.9%

| E9.4 | wt % |
|---|---|
| water phase: | |
| G-IPA (60%) and 2,4-D at ratio 1:1 | 50 |
| Synperonic A7 | 0.5 |
| Arabic Gum | 1.6 |

| E9.4 | wt % |
|---|---|
| oil phase: | |
| TMXDI | 5 |
| Cythane 3174 | 0.5 |
| Agrimer AL 22 | 4 |
| Room* to add Adjustment Mixture A | 10 |
| solvesso 200 to 100% | 23.4 |
| Diethylentriamin in water (20%) | 5 |

Average Particle size: 8.4 μm
Separation of oil/water phase after 2 weeks at 54° C.: no
Unencapsulated a.i.: below limit of detection (0.01%)

In all this formulations, we have obtained convenient microcapsules with novel formulas, while not keeping free the water phase from all the components but the a.i. We can perform this with Glyphosate isopropylammonium salt and 2,4-D sodium, since none of the components added in the water phase react with the a.i. While the preferred embodiments of this invention are those that keep the water phase only for the active ingredient(s), this does not mean that other advantages of the invention can be used when adding wall forming materials in the water phase (in this case, the exactly same Adjustment Mixture A of Example 1 has been used to obtain perfectly stable formulations of microcapsules, a logistical advantage).

EXAMPLE 10

Water Dispersable Granules of Thifensulfuron-Methyl and RPμ Containing Glyphosate Ammonium A formulation (water based) according Example 5 was made, with the substitution of fluorocloridone by thifensulfuron-methyl and acifluorfen sodium by glyphosate ammonium (E10.1). At the end of the process, in order to allow the spray-dry process, it was added 10% (with respect total weight of formed E10.1) of sodium dioctylsulfosuccinate wetter was added and also 1% of sodium stearic methyl tauride dispersant. To this amount, an Adjustment Mixture AM-DRPμ for allowing the spray dry process was used, consisting in 48% of cyclodextrin, 2% of Arbocel™, 25% CMC (carboxymethylcellulose) and 25% dextrin. 30% over the 1000 g (300 g) of this mixture was added directly to the spray chamber and then the product was sprayed dried, yielding WDG as shown in FIG. 3.

EXAMPLE 11

A series of unsuccessful tests are represented by the following formulas. The resulting microencapsulated products did not satisfied the minimum requirements for a homogeneous distributed particle size or the stability was poor (separation of oil from water after 4 days at 54° C.). In most cases, the combination of wall forming materials produced a very fast reaction in an uncontrollable way.

| Ingredient | parts | CEI | I | II | III | IV | V | VI | VII | VIII | IX | X |
|---|---|---|---|---|---|---|---|---|---|---|---|---|
| water phase: | | | | | | | | | | | | |
| water | 25 | 13 | 25 | 25 | 25 | 25 | 25 | 25 | 25 | 25 | 25 | 25 |
| G-IPA (50 wt %) | 25 | 25 | 25 | 25 | 25 | 25 | 25 | 25 | 25 | 25 | 25 | 25 |
| Synperonic A7 | 0.5 | — | 0.5 | 0.5 | 0.5 | 0.5 | 0.5 | 0.5 | 0.5 | 0.5 | 0.5 | 0.5 |
| Allantoin | 0.5 | — | 0.5 | 0.5 | 0.5 | 0.5 | 0.5 | 0.5 | 0.5 | 0.5 | 0.5 | 0.5 |

-continued

| Ingredient | parts | CEI | I | II | III | IV | V | VI | VII | VIII | IX | X |
|---|---|---|---|---|---|---|---|---|---|---|---|---|
| WS-351-380 | — | 13 | — | — | — | — | — | — | — | — | — | — |
| Maleic anhydrid (50%) | 1 | — | 1 | 1 | 1 | 1 | 1 | 1 | 1 | 1 | 1 | 1 |
| oil phase: | | | | | | | | | | | | |
| Aristol A | 3 | 3 | — | — | — | — | — | — | — | — | — | — |
| Igepal CA-630 | 3 | 3 | — | — | — | — | — | — | — | — | — | — |
| Dynomin UI 20E (50%) | 10 | — | 10 | 10 | 10 | 10 | 10 | — | — | — | — | — |
| Cymel 1170 (50%) | 1 | — | 1 | 1 | 1 | 1 | 1 | — | — | — | — | — |
| Arlatone T | 3 | — | 3 | — | — | — | — | — | — | — | — | — |
| Agrimer AL 22 | 3 | — | — | — | — | — | — | 3 | — | — | — | — |
| VEMA ES 43 | 3 | — | — | — | — | — | — | — | 3 | — | — | 3 |
| Synperonic PE/L 61 | 3 | — | — | — | — | — | — | — | — | 3 | — | — |
| Agrimer VA-3I | 3 | — | — | — | — | — | — | — | — | — | 3 | — |
| Atlas G-1086 | 3 | — | — | 3 | — | — | — | 3 | 3 | 3 | 3 | 3 |
| Agrimer VA-5E | 3 | — | — | — | — | — | — | 3 | 3 | 3 | 3 | 3 |
| Span 20 | 3 | — | — | — | — | 3 | — | 3 | 3 | 3 | 3 | 3 |
| Synperonic PE/L42 | 2 | — | — | — | 3 | — | — | 2 | 2 | 2 | 2 | 2 |
| Synperonic PE/L121 | 3 | — | — | — | — | — | 3 | — | — | — | — | — |
| Solvent 450 | 43 | 43 | | | | | | | | | | |
| solvesso 200 | 34 | — | 34 | 34 | 34 | 34 | 34 | 45 | 45 | 45 | 45 | 45 |

In CEI, it was found 10% of unencapsulated Glyphosate isopropylammonium. Further, rests of formaldehyde were detectable at 0.008%, meaning that the water soluble resin could not react in full, or at least total consumption of toxic formaldehyde was not achieved.

The presence of formaldehyde in all the Examples 1-10 of this invention was tested and we could not detect any residual presence of isocyanates (via derivatization and HPLC-UV analysis) (0.0001% limit of detection) either from formaldehyde (0.001% limit of detection).

The invention claimed is:

1. Microcapsules for controlled release of water soluble or dispersible compounds, wherein each microcapsule has a polymeric wall comprising an in-situ reaction product of oil soluble materials comprising:
   (i) at least one glycoluril resin, and
   (ii) at least one isocyanate,
wherein the ratio of (ii) to (i) is at the most 20:1 and at least 1:2,
wherein the average size of the microcapsules is from 0.1 μm to 25 μm, and
wherein the size percentile 90 of the microcapsules is at the most 100 μm, when measured in dispersion in water in a laser diffraction apparatus.

2. Microcapsules according to claim 1, wherein each microcapsule has one or more microencapsulated compounds therein and wherein each microcapsule has a polymeric wall comprising a reaction product of:
   (i) a glycoluril resin, and
   (ii) an aliphatic polyisocyanate resin,
wherein the reaction product is produced by a polymerization reaction using at least one catalyst selected from the group consisting of: (a) a polycyclic azo compound and (b) a non-nitrogenated catalyst,
wherein the concentration of the one or more micronencapsulated compounds in a core water phase during the polymerization reaction is below a solubility in water limit at 20° C. of each of the one or more micronencapsulated compounds,
wherein the average size of the microcapsules is from 0.1 μm to 25 μm, and
wherein the size percentile 90 of the microcapsules is at the most 50 μm, when measured in dispersion in water in a laser diffraction apparatus.

3. Microcapsules according to claim 1, wherein each of the microcapsules contains one or more microencapsulated water soluble compounds selected from the group consisting of: acifluorfen-sodium, ammonium sulfamate, asulam-sodium, aviglycine hydrochloride, potassium bicarbonate, sodium bicarbonate, bilanafos-sodium, bispyribac-sodium, borax, bromoxynil heptanoate, sec-butylamine, cartap hydrochloride, chlormequat chloride, sodium chloroacetate, clofencet-potassium, clopyralid-olamine, copper sulfate, 2,4-D-dimethylammonium, 2,4-D-sodium, dalapon-sodium, 2,4-DB-sodium, dicamba, dichlorprop-potassium, dikegulac-sodium, dinoterb-diolamine, diquat dibromide, diquat dichloride, ferrous sulfate, flucarbazone-sodium, flupropanate-sodium, formaldehyde, formetanate hydrochloride, fosamine-ammonium, fosetyl-aluminium, fosthiazate, gibberellic acid, glufosinate-ammonium, glyphosate-isopropylammonium, glyphosate-trimesium, glyphosate-sodium, glyphosate-ammonium, glyphosate, guazatine acetates, GY-81, hexazinone, 8-hydroxyquinoline sulfate, hymexazol, imazalil sulfate, imazapyr, imazaquin-ammonium, iminoctadine triacetate, iodosulfuron-methyl-sodium, ioxynil-sodium, ioxynil, kasugamycin hydrochloride hydrate, maleic hydrazide, maleic hydrazide potassium salt, MCPA-sodium, MCPA-sodium, mepiquat chloride, mercuric chloride, mesosulfuron-methyl, mesotrione, metalaxyl, metalaxyl-M, metam-sodium, methamidophos, methomyl, methaldehyde, naptalam-sodium, nicotine, sodium o-nitrophenolate, sodium p-nitrophenolate, sodium 5-nitroguaiacolate, paraquat dibromide, paraquat dichloride, sodium pentachlorophenoxide, sodium 2-phenylphenoxide, phloxine, picloram-triisopropanolammonium, picloram-potassium, propamocarb hydrochloride, propoxycarbazone-sodium, pyrithiobac-sodium, streptomycin sesquisulfate, strychnine, 2,3,6-TBA, trichloroacetic acid, TCA-sodium, thiocyclam hydrogen oxalate, trifloxysulfuron-sodium, validamycin, chlordimeform hydrochloride, chlorphonium chloride, dehydroacetic acid, 2-methoxyethylmercury chloride, natamycin, potassium cyanate, prothiocarb hydrochloride, sodium fluoride, sodium hexafluorosilicate, including any water soluble forms of these compounds, either alone or in combination, and in any isomeric or stereochemical form.

4. Microcapsules according to claim 1, wherein each microcapsule has one or more microencapsulated compounds therein in a core water phase, wherein each of the microencapsulated compounds are either: (a) water soluble compounds that do not precipitate due to saturation because of reaching the limit concentration in the core water phase or (b)

water dispersible compounds that are dispersible in water and a member of the group consisting of: drugs or medicines, living or dead organisms in any physiological state including spores or pollen, such as mycoplasmas, fungi, bacteria, cells, stem cells, cells for xenotransplantation, virus, viroids, prions, yeasts, plants, or genetic material, amino acids, proteins, nucleic acids, DNA, RNA, vaccines and compounds directed for feeding purposes.

5. Microcapsules according to claim 1, wherein the microcapsules are in a dry or flowable form.

6. Microcapsules according to claim 5, wherein the microcapsules are combined with oil soluble agrochemicals present in a dry or flowable form.

7. Microcapsules according to claim 5, wherein the microcapsules are dispersed and surrounded by an external water phase with the aid of surface active compounds.

8. Microcapsules according to claim 7, wherein the microcapsules are dispersed and surrounded by an external oil phase, thereby making a formulation comprising the microcapsules emulsifiable in water, with the aid of surface active compounds.

9. A composition comprising water dispersible granules containing microcapsules according to claim 1.

10. A composition comprising a suspension concentrate plus capsule suspension containing microcapsules according to claim 1.

11. A composition comprising a combination of an emulsion concentrate plus capsule suspension, containing microcapsules according to claim 1.

12. A process comprising the following steps:
  (a) providing an aqueous phase comprising water and one or more compounds to be microencapsulated;
  (b) providing an oil phase comprising an oil, a nonpolar solvent substantially insoluble in water, and wall forming materials comprising: one or more glycoluril resins, one or more aliphatic isocyanates and one or more oil soluble surface active ingredient(s);
  (c) emulsifying the aqueous phase into the oil phase, at a temperature of 40 to 60° C., this step initiating an in situ polymerization reaction of the wall forming materials onto water droplets of the aqueous phase; and
  (d) raising the temperature for curing to 60-100° C., wherein the process produces the microcapsules of claim 1, each of the microcapsules having microencapsulated within a polymeric wall of the microcapsule a water phase containing one or more water soluble compounds.

13. The process according to claim 12, wherein the aqueous phase comprises active ingredients and/or surfactants that are dispersed in the water of the aqueous phase and that are substantially insoluble in the oil phase.

14. The process according to claim 12, wherein at least one compound of the one or more compounds to be microencapsulated is biologically active and does not lose its biological activity due to the reaction with any compound or mixture of compounds present in the process, or to the conditions of the process, including temperature degradation and reactions with the wall forming materials.

15. The process according to claim 12, wherein at least one compound of the one or more compounds to be microencapsulated is an agrochemical active ingredient.

16. The process according to claim 12, wherein at least one compound of the one or more compounds to be microencapsulated is a cosmetic, pharmaceutical, medicinal, nutraceutic, or biotechnologically-obtained active ingredient.

17. The process according to claim 12, wherein at least one compound of the one or more compounds is a biologically active agrochemical and is selected from the group consisting of: acephate, acetamiprid, acifluorfen-sodium, acrolein, aldicarb, alloxydim, amicarbazone, amidosulfuron, amitrole, ammonium sulfamate, asulam, asulam-sodium, aviglycine, aviglycine hydrochloride, azimsulfuron, bensulfuron-methyl, bentazone, potassium bicarbonate, sodium bicarbonate, bilanafos, bilanafos-sodium, bispyribac-sodium, blasticidin-S, borax, bromoxynil heptanoate, bronopol, butocarboxim, butoxycarboxim, sec-butylamine, carbetamide, cartap hydrochloride, chloralose, chlormequat chloride, sodium chloroacetate, chlorsulfuron, cinosulfuron, clofencet-potassium, clopyralid-olamine, clopyralid, copper sulfate, cyanamide, cyromazine, 2,4-D-dimethylammonium, 2,4-D-sodium, 2,4-D, 2,4-D-trolamine, dalapon-sodium, daminozide, dazomet, 2,4-DB-sodium, demeton-S-methyl, dicamba, dichlormid, dichlorprop-potassium, dichlorprop, dichlorvos, diclofop, dicrotophos, dicyclanil, difenzoquat metilsulfate, diflufenzopyr, dikegulac-sodium, dimethipin, dimethoate, dinotefuran, dinoterb-diolamine, diquat dibromide, DNOC, endothal, ethephon, ethoxysulfuron, ethylene dibromide, fenoxanil, fenoxaprop-P, ferrous sulfate, flonicamid, florasulam, flucarbazone-sodium, flupropanate-sodium, fluoroxypyr, fomesafen, foramsulfuron, formaldehyde, formetanate hydrochloride, fosamine-ammonium, fosetyl-aluminium, fosthiazate, gibberellic acid, glufosinate-ammonium, glyphosate-isopropylammonium, glyphosate-trimesium, glyphosate-sodium, glyphosate-ammonium, glyphosate, guazatine acetates, GY-81, hexazinone, hydrogen cyanide, 8-hydroxyquinoline sulfate, hymexazol, imazalil sulfate, imazamox, imazapyr, imazaquin-ammonium, iminoctadine triacetate, iodosulfuron-methyl-sodium, ioxynil-sodium, ioxynil, kasugamycin hydrochloride hydrate, maleic hydrazide, maleic hydrazide potassium salt, MCPA-sodium, MCPA-sodium, mepiquat chloride, mercuric chloride, mesosulfuron-methyl, mesotrione, metalaxyl, metalaxyl-M, metam-sodium, methamidophos, methomyl, methylarsonic acid, DSMA, MSMA, methyl bromide, methyl iodide, methyl isothiocyanate, metosulam, metsulfuron-methyl, mevinphos, monocrotophos, nabam, naptalam-sodium, nicotine, nitenpyram, sodium o-nitrophenolate, sodium p-nitrophenolate, sodium 5-nitroguaiacolate, oxadixyl, oxamyl, oxasulfuron, oxydemeton-methyl, paraquat dichloride, sodium pentachlorophenoxide, phenylmercury acetate, sodium 2-phenylphenoxide, phosphamidon, phosphine, phosphonic acid, picloram-triisopropanolammonium, picloram-potassium, pirimicarb, polyoxorim, polyoxin B, primisulfuron-methyl, propamocarb hydrochloride, propamocarb, propoxycarbazone-sodium, prosulfuron, pyrithiobac-sodium, pyroquilon, quinmerac, rimsulfuron, sabadilla, sethoxydim, sodium chlorate, spiroxamine, streptomycin sesquisulfate, strychnine, sulfentrazone, 2,3,6-TBA, trichloroacetic acid, TCA-sodium, thiamethoxam, thifensulfuron-methyl, thiocyclam hydrogen oxalate, thiofanox, tralkoxydim, triasulfuron, trichlorfon, triclopyr, trifloxysulfuron-sodium, triflumizole, triflusulfuron-methyl, trimedlure, trimethacarb, trinexapac-ethyl, trinexapac, validamycin, vamidothion, warfarin, acrylonitrile, aldoxycarb, allidochlor, ampropylfos, anabasine, arsenous oxide, buthidazole, chlordimeform, chlordimeform hydrochloride, chlorphonium chloride, crimidine, cycloheximide, dehydroacetic acid, demephion, demephion-O, demephion-S, demeton-S-methylsulphon, dimefox, dioxacarb, disul, disul-sodium, DKA-24, drazoxolon, EI 1642, etacelasil, ethidimuron, ethidimuron, ethyl hexanediol, fenaminosulf, fenuron, fenuron-TCA, fluothiuron, fosthietan, glyphosine, glyphosine, 2-hydrazino ethanol, isolane, LS830556, 2-methoxyethylmercury chloride, MG 191, natamycin, nithiazine, phosfolan, potassium cyanate, prothiocarb, prothiocarb hydrochloride, schradan, sodium fluoride, sodium hexafluorosilicate and TEPP.

18. The process according to claim 12, wherein the oil phase comprises a dibutyl tin catalyst.

19. The process according to claim 12, wherein the oil phase contains a non-nitrogenated proton transfer catalyst if a catalyst is not added during step (c), wherein during step (d) an oil soluble aza catalyst of the type DBU is added when the polymerization reaction has already begun, about 5-30 minutes after the addition of the water phase to the oil phase if the oil phase does not contain the non-nitrogenated proton transfer catalyst, wherein the process comprises the following step: (e) adding coformulants to form a functionally acceptable agricultural formulation, and wherein the process produces a composition comprising microcapsules that microencapsulate a water soluble or water dispersible biologically active compound within a wall made of a reaction product of at least a glycoluril resin and an isocyanate.

20. A composition produced according to the process of claim 19.

21. The composition of claim 19, wherein binders and coformulants are added during step (e) to form a water dispersible granules formulation.

22. A composition produced by the process of claim 12, wherein the oil phase contains at least one compound selected from the group consisting of: amidosulfuron, bensulfuron-methyl, chlorimuron, chlorsulfuron, cinosulfuron, cyclosulfamuron, ethametsulfuron-methyl, ethoxysulfuron, flazasulfuron, Flupyrsulfuron-methyl, foramsulfuron, halosulfuron-methyl, imazosulfuron, iodosulfuron-methyl, mesosulfuron, metsulfuron-methyl, nicosulfuron, oxasulfuron, primisulfuron-methyl, prosulfuron, pyrazosulfuron-methyl, rimsulfuron, sulfosulfuron, thifensulfuron-methyl, triasulfuron, tribenuron-methyl, trifloxysulfuron, triflusulfuron-methyl, tritosulfuron, any derivative of these compounds including any alkyl derivatives, dealkylated derivatives and/or oil soluble salts thereof.

23. A composition produced by the process of claim 12, wherein the microcapsules microencapsulate one or more water soluble sulfonylurea salts.

24. A composition produced by the process of claim 12, wherein, apart from a water soluble or water dispersible microencapsulated agrochemical, at least one other compound is dispersed into the oil phase.

25. A composition produced by the process of claim 12, wherein the water phase contains a water soluble microencapsulated agrochemical selected from the group consisting of: glyphosate, glufosinate, glufosinate, paraquat, diquat, chlormequat and 2,4-D, in any form and wherein the oil phase contains diflufenican or an aryoxyphenoxypropionate.

26. A composition produced by the process of claim 12, wherein the water phase contains a water soluble microencapsulated agrochemical selected from the group consisting of: glyphosate, glufosinate, sulfosate in any form and wherein the oil phase contains nicosulfuron.

27. A composition produced by the process of claim 12, wherein the water phase contains a water soluble microencapsulated agrochemical that is a "quat" herbicide and wherein the oil phase contains a sulfonylurea or sulfonamide herbicide.

28. A composition produced by the process of claim 12, wherein the water phase contains one or more water soluble microencapsulated agrochemicals of the group consisting of: glyphosate, glufosinate and sulfosate, in any form, and wherein the oil phase contains lactofen.

29. A composition comprising:
   (a) reverse phase microcapsules (RPµ) containing a watery core comprising at least one water soluble active ingredient, and
   (b) normal phase microcapsules (NPµ) containing an oily core comprising at least one oil soluble active ingredient,
wherein each of the reverse phase microcapsules are microcapsules for controlled release of water soluble or dispersible compounds, and wherein each microcapsule has a polymeric wall comprising an in-situ reaction product of oil soluble materials comprising:
   (i) at least one glycoluril resin, and
   (ii) at least one isocyanate,
wherein the ratio of (ii) to (i) is at the most 20:1 and at least 1:2,
wherein the average size of the microcapsules is from 0.1 µm to 25 µm, and
wherein the size percentile 90 of the microcapsules is at the most 100 µm, when measured in dispersion in water in a laser diffraction apparatus.

30. The composition of claim 29, wherein the composition is in the form of a water-based formulation with suspended RPµ and NPµ therein.

31. The composition of claim 29, wherein the composition is in the form of an oil-based formulation with suspended microcapsules RPµ and NPµ therein.

32. The composition of claim 29, wherein the composition is in the form of water dispersible granules.

33. The composition of claim 29, wherein the composition is a suspension concentrate.

34. The composition of claim 29, wherein the composition is an emulsion concentrate.

35. The composition of claim 29, wherein the composition is an oil dispersion.

36. The composition of claim 29, wherein the water soluble active ingredient and the oil soluble active ingredient have different biological effects, and wherein together the water soluble active ingredient and the oil soluble active ingredient are a combination selected from the group consisting of: a fungicide and a herbicide combination, a fungicide and an insecticide combination, an insecticide and a herbicide combination, an insecticide and a plant growth regulator combination, and an insecticide and a semiochemical combination.

37. A process of producing the composition of claim 29, wherein the process comprises the following steps:
   (a) obtaining an oil-based suspension of microcapsules RPg,
   (b) obtaining a water-based suspension of microcapsules NPg, and alternatively
   (c) emulsifying the oil-based suspension into the water-based suspension with the use of a surfactant or mixture of surfactants at a concentration of 1-50% with respect to the total weight of water-based suspension with an HLB value of 7-14, or
   (d) emulsifying the water-based suspension into the oil-based suspension with the use of a surfactant or mixture of surfactants at a concentration of 1-50% with respect to the total weight of water-based suspension with an HLB value of 1-7.

* * * * *

UNITED STATES PATENT AND TRADEMARK OFFICE
CERTIFICATE OF CORRECTION

PATENT NO. : 8,337,900 B2  
APPLICATION NO. : 12/225889  
DATED : December 25, 2012  
INVENTOR(S) : Victor Casana Giner, Miguel Gimeno Sierra and Barbara Gimeno Sierra Page 1 of 1

It is certified that error appears in the above-identified patent and that said Letters Patent is hereby corrected as shown below:

Title Page, Item [76], Inventors: replace "Victor CasanGiner" with "Victor Casana Giner"

Signed and Sealed this
Nineteenth Day of February, 2013

Teresa Stanek Rea
*Acting Director of the United States Patent and Trademark Office*